United States Patent [19]

Hamer et al.

[11] Patent Number: 5,621,114

[45] Date of Patent: Apr. 15, 1997

[54] METHOD FOR PREPARING 1, 2, 3, 3A, 8, 8A-HEXAHYDRO-3A, 8 (AND 1, 3A, 8)—DI (AND TRI) METHYLPYRROLO[2,3-B] INDOLES

[75] Inventors: Richard L. Hamer, Far Hills; Grover C. Helsley, Pluckemin; Edward J. Glamkowski, Warren; Yulin Chiang, Convent Station, all of N.J.

[73] Assignee: Hoechst Marion Roussel, Inc., Kansas City, Mo.

[21] Appl. No.: 479,197

[22] Filed: Jun. 7, 1995

Related U.S. Application Data

[63] Continuation of Ser. No. 967,534, Oct. 28, 1992, Pat. No. 5,541,216, which is a continuation of Ser. No. 828,751, Jan. 31, 1992, abandoned, which is a continuation of Ser. No. 252,309, Oct. 3, 1988, abandoned, which is a division of Ser. No. 49,894, May 15, 1987, Pat. No. 4,791,107, which is a continuation-in-part of Ser. No. 885,991, Jul. 16, 1986, abandoned.

[51] Int. Cl.⁶ ................................ C07D 487/04
[52] U.S. Cl. ................................ 548/429
[58] Field of Search ........................ 548/429

[56] References Cited

U.S. PATENT DOCUMENTS

| | | |
|---|---|---|
| 2,678,899 | 5/1954 | Miller et al. |
| 2,909,530 | 10/1959 | Rudner et al. |
| 3,457,268 | 7/1969 | Frey et al. |
| 3,547,945 | 12/1970 | Frey et al. |
| 3,547,947 | 12/1970 | Frey et al. |
| 3,551,450 | 12/1970 | Frey et al. |
| 3,897,451 | 7/1975 | Gassman |
| 4,278,667 | 7/1981 | Madison et al. |
| 4,680,172 | 7/1987 | Leeson |
| 4,760,083 | 7/1988 | Myers et al. |
| 4,765,985 | 8/1988 | Leeson |
| 4,791,107 | 12/1988 | Hamer et al. |
| 4,831,155 | 5/1989 | Brufani et al. |
| 4,857,648 | 8/1989 | Broger et al. |
| 4,900,748 | 2/1990 | Brossi et al. |
| 4,914,102 | 4/1990 | Glamkowski et al. |
| 4,937,341 | 6/1990 | Glamkowski et al. |
| 4,971,992 | 11/1990 | Glamkowski et al. |
| 4,978,673 | 12/1990 | Meroni et al. |
| 4,983,616 | 1/1991 | O'Malley et al. |
| 5,077,289 | 12/1991 | Glamkowski et al. |
| 5,081,117 | 1/1992 | Glamkowski et al. |
| 5,091,541 | 2/1992 | O'Malley et al. |
| 5,171,750 | 12/1992 | Brossi et al. |
| 5,173,497 | 12/1992 | Flanagan |
| 5,177,101 | 1/1993 | Glamkowski et al. |
| 5,187,165 | 2/1993 | Hamer et al. |
| 5,206,260 | 4/1993 | Hichens et al. |
| 5,216,017 | 6/1993 | Allen et al. |
| 5,260,452 | 11/1993 | Glamkowski et al. |

FOREIGN PATENT DOCUMENTS

| | | |
|---|---|---|
| 0154864A1 | 9/1985 | European Pat. Off. |
| 0253372A2 | 1/1988 | European Pat. Off. |
| 0298202A1 | 1/1989 | European Pat. Off. |
| 0354594A2 | 2/1990 | European Pat. Off. |
| 0513703A2 | 11/1992 | European Pat. Off. |
| 2005259 | 4/1979 | United Kingdom |
| WO92/00072 | 1/1992 | WIPO |

OTHER PUBLICATIONS

Atack et al., Comparative Inhibitory Effects of Various Physostigmine Analogs Against Acetyl- and Butyrylcholinesterases, J. Pharmacol. Exp. Therapeutics, 249(1): 194–202 (1989).

Bartolini et al., Eseroline: A New Antinociceptive Agent Derived from Physostigmine with Opiate Receptor Agonist Properties. Experimental In Vivo and In Vitro Studies on Cats and Rodents, Neurosci. Lett., 25: 179–183 (1981).

Berge et al., Pharmaceutical Salts, J. Pharm. Sci., 66: 1–19 (1977).

(List continued on next page.)

*Primary Examiner*—Robert W. Ramsuer
*Attorney, Agent, or Firm*—Finnegan, Henderson, Farabow, Garrett & Dunner, L.L.P.

[57] ABSTRACT

There are described compounds of the formula

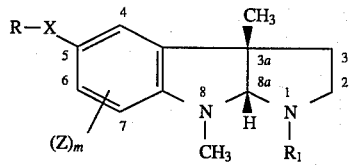

where
(a) X is O or S;
(b) R is H, loweralkyl,

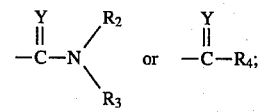

where Y is O or S; $R_2$ is alkyl, cycloalkyl, bicycloalkyl, cycloalkenyl, aryl, arylloweralkyl, heteroaryl or heteroarylloweralkyl, $R_3$ is H or alkyl, or the group —$NR_2R_3$ taken as a whole is 1-pyrrolidinyl, 1-piperidinyl, 4-morpholinyl, 4-thiomorpholinyl, 1-piperazinyl, 4-methyl-1-piperazinyl or 2-(2,6-dichlorophenylimino)-1-imidazolidinyl) and $R_4$ is hydrogen, loweralkyl, arylloweralkyl, diarylloweralkyl, aryl or heteroaryl,
(c) m is 1 or 2;
(d) each Z is independently H, loweralkyl, halogen, nitro, —$NH_2$, loweralkylcarbonylamino, arylcarbonylamino, loweralkoxycarbonylamino or loweralkylamino, and
(e) $R_1$ is H, loweralkyl, arylloweralkyl, heteroarylloweralkyl, cycloalkylmethyl or loweralkenylmethyl, with the proviso that when X is O, m is 1, Z is H and $R_1$ is methyl, R is not —$CONHCH_3$, —$CONHC_6H_5$, hydrogen, methyl or ethyl, and that when X is O, m is 1 and Z and $R_1$ are both hydrogen, R is not hydrogen or methyl, and pharmaceutically acceptable acid addition salts thereof which are useful as memory-enhancing and analgesic agents.

4 Claims, No Drawings

OTHER PUBLICATIONS

Bores et al., HP 290: A Potent, Orally Active Cholinesterase Inhibitor for the Treatment of Alzheimer's Disease, Soc. Neurosci. Abstr. 17(1): 699 (1991).

Brossi et al., Chemical Abstracts 109: 740 (1988), Abstract Nos. 190632x and 190633y.

Brzostowska et al., Phenylcarbamates of (–)–Eseroline, (–)–N[1]–Noreseroline and (–)–Physovenol: Selective Inhibitors of Acetyl and, or Butyrylcholinesterase, Med. Chem. Res., 2: 238–246 (1992).

Brufani et al., Anticholinesterase Activity of a New Carbamate, Heptylphysostigmine, in View of Its Use in Patients with Alzheimer–type Dementia, Eur. J. Biochem., 157:115–120 (1986).

Chemical Abstracts, Section 25, Benzene, Its Derivatives, And Condensed Benzenoid Compounds, 108(25): 535–543 (1988).

Colvin, Silicon in Organic Synthesis, Butterworths Monographs in Chemistry and Chemical Engineering, Chapter 10, Butterworths (London) (1981).

Ellis et al., Studies on Physostigmine and Related Substances[1], III. Breakdown Products of Physostigmine; Their Inhibitory Effect on Cholinesterase and Their Pharmacological Action, J. Pharm. Exp. Ther., 79: 309–319 (1943).

Galli et al., Inhibition of [³H]naloxone Binding in Homogenates of Rat Brain by Eseroline, a Drug, with Analgesic Activity, Related to Physostigmine, J. Pharm. Pharmacol. (Communications), 31: 784–786 (1979).

Giacobini et al., Pharmacokinetics and Pharmacodynamics of Physostigmine After Intravenous Administration in Beagle Dogs, Neuropharmacology, 831–836 (1987).

Gorman et al., Comparison of the Cardiovascular Effects of HP 290 and Heptylstigmine (HEP), New Cholinesterase Inhibitors in the Treatment of Alzheimer's Disease, Meeting Abstract No. 7210, FASEB Annual Meeting, Atlanta, GA, Apr., 1991.

Gould, Salt Selection for Basic Drugs, Int. J. Pharmaceutics, 33: 201–217 (1986).

Hamer et al., HP 290: A New, Potent Cholinesterase Inhibitor for the Treatment of Alzheimer's Disease, Meeting Abstract No. 74, American Chemical Society Division of Medicinal Chemistry, Atlanta, GA, Apr., 1991.

Hamer et al., Chemical Abstracts 108: 596 (1988), Abstract No. 221937m.

Howard et al., HP 290: A Potential Alzheimer's Therapeutic Agent with Reduced Cardiovascular Liability, Soc. Neurosci. Abstr., 17(1): 699 (1991).

Isaksson and Kissinger, Metabolism of Physostigmine in Mouse Liver Microsomal Incubations Studied by Liquid Chromatography with Dual–Electrode Amperometric Detection, J. Chromatography, 419: 165–175 (1987).

Julian and Pikl, Studies in the Indole Series. IV. The Synthesis of d,l–Eserethole, J. Am. Chem. Soc., 57: 563–566 (1935).

Julian and Pikl, Studies in the Indole Series, V. The Complete Synthesis of Physostygmine (Eserine), J. Am. Chem. Soc., 57: 755–757 (1935).

King and Robinson, Experiments on the Synthesis of Physostigmine (Eserine). Part XI. The Later Phases of the Synthetical Investigations, J. Chem. Soc., 755–759 (1935).

Merck Index, The, Eleventh Edition (1989), pp. 1172–1173.

New Candidates for Treating Alzheimer's, C & E News, Apr. 29, 1991, p. 28.

Polonovski, Bull. Chem. Soc. France, 19: 47–59 (1916).

Polonovski, Chemical Abstracts, 10: 1329 (1916).

Robinson, Alkaloids of the Calabar Bean, in: *The Alkaloids*, Manske, ed., Chapter 5, pp. 383–400 (1968).

Robinson, Synthesis of dl–Eseramine[1], Chem. & Ind., Jan. 9, 1985, pp. 87–88.

Robinson and Robinson, The Anti–Acetylcholinesterase Activities of the Alkaloids of Physostigma veneosum Seeds, J. Pharm. Pharmac., 20(Suppl.): 213S–217S (1968).

Roth and Fenner, in: Pharmazeutische Chemie III: Arzneistoffe Struktur–Bioreaktivitat–Wirkungsbezogene Eigenschaften, Verlag (Stuttgart), 1988, pp. 390–395.

Salway, Researches on the Constitution of Physostigmine Part I, J. Chem. Soc., 101: 978–989 (1912).

Schonenberger and Brossi, Fragmentation of Optically Active (1–Phenylethyl)—and (1–Naphthylethyl) ureas in Refluxing Alcohols: Easy Preparation of Optically Active Amines of High Optical Purity, Helvetica Chimica Acta, 69: 1486–1497 (1986).

Schonenberger et al., Comparison of (–)–Eseroline with (+)–Eseroline and Hihydroseco Analogues in Antinociceptive Assays: Confirmation of Rubreserine Structure by X–ray Analysis, J. Med. Chem., 29: 2268–2273 (1986).

Schonenberger et al., Preparation of Optically Active Secondary Amines by Thermal Decomposition of (Methylbenzyl)urea Analogs: Absolute Configuration of (+)–and (–)–Mecamylanime, Helvetica Chimica Acta, 69: 283–287 (1986).

Sibi et al., The Directed Ortho Lithiation of O–Aryl Carbamates. An Anionic Equivalent of the Fries Rearrangement, J. Org. Chem., 48: 1935–1937 (1983).

Somani and Khalique, Pharmacokinetics and Pharmacodynamics of Physostigmine in the Rat After Intravenous Administration, Drug Metabolism and Disposition, 15(5): 627–633 (1987).

Somani, Pharmacokinetics and Pharmacodynamics of Physostigmine in the Rat After Oral Administration, Biopharmaceutics & Drug Disposition, 10: 187–203 (1989).

Stern et al., Effects of Oral Physostigmine in the Alzheimer's Disease, Ann. Neurol., 22: 306–310 (1987).

Sumimoto Pharm. Co., Ltd. (Japan), SM–10888: Agent for Cognition Disorders; Acetylcholinesterase Inhibitor, Drugs of the Future, 16(1): 33–36 (1991).

Trommer et al., Thioeserin, das Thioanalogon des Eserine, Arch. Pharm., 309: 631–638 (1976).

Unni and Somani, Hepatic and Muscle Clearance of Physostigmine in the Rat, Drug Metabolism and Disposition, 14(2): 183–289 (1986).

Unni et al., Kinetics of Cholinesterase Inhibition by Eptastigmine in Man, Eur. J. Clin. Pharmacol., 41:83–84 (1991).

Yu et al., Synthesis and Anticholinesterase Activity of (–)–N[1]–Norphysostigmine, (–)–Eseramine, and Other N(1)–Substituted Analogues of (1)–Physostigmine, J. Med. Chem., 31(12): 2297–2300 (1988).

Yu and Erossi, Practical Synthesis of Unnatural (+)–Physostigmine and Carbamate Analogues, Heterocycles, 27(3): 745–750 (1988).

METHOD FOR PREPARING 1, 2, 3, 3A, 8, 8A-HEXAHYDRO-3A, 8 (AND 1, 3A, 8)—DI (AND TRI) METHYLPYRROLO[2,3-B] INDOLES

This is a continuation of application Ser. No. 07/967,534, filed Oct. 28, 1992, U.S. Pat. No. 5,541,216 which is a continuation of application Ser. No. 07/828,751, filed Jan. 31, 1992 (now abandoned), which is a continuation of application Ser. No. 07/252,309, filed Oct. 3, 1988 now abandoned; which is a division of application Ser. No. 07/049,894, filed May 15, 1987, which is now U.S. Pat. No. 4,791,107; which in turn is a continuation-in-part of application Ser. No. 06/885,991, filed Jul. 16, 1986, which is now abandoned.

The present invention relates to compounds of the formula,

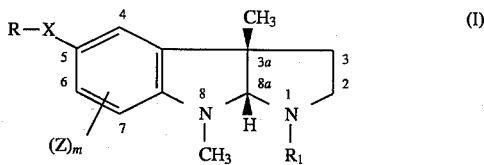

where
(a) X is O or S;
(b) R is H, loweralkyl,

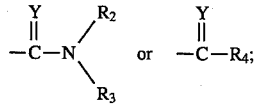

where Y is O or S; $R_2$ is alkyl, cycloalkyl, bicycloalkyl, cycloalkenyl, aryl, arylloweralkyl, heteroaryl or heteroarylloweralkyl, $R_3$ is H or alkyl, or the group —$NR_2R_3$ taken as a whole is 1-pyrrolidinyl, 1-piperidinyl, 4-morpholinyl, 4-thiomorpholinyl, 1-piperazinyl, 4-methyl-1-piperazinyl or 2-(2,6-dichlorophenylimino)-1-imidazolidinyl) and $R_4$ ts hydrogen, loweralkyl, arylloweralkyl, diarylloweralkyl, aryl or heteroaryl,
(c) m is 1 or 2;
(d) each Z is independently H, loweralkyl, halogen, nitro, —$NH_2$, loweralkylcarbonylamino, arylcarbonylamino, loweralkoxycarbonylamino or loweralkylamino, and
(e) $R_1$ is H, loweralkyl, arylloweralkyl, heteroarylloweralkyl, cycloalkylmethyl or loweralkenylmethyl,
with the proviso that when X is O, m is 1, Z is H and $R_1$ is methyl, R is not —$CONHCH_3$, —$CONHC_6H_5$, hydrogen, methyl or ethyl, and that when X is O, m is 1 and Z and $R_1$ are both hydrogen, R is not hydrogen or methyl, which are useful as memory-enhancing and analgesic agents; pharmaceutical compositions comprising an effective amount of such a compound; a method of treating a patient in need of memory enhancement comprising the administration of such a compound to the patient and a method of relieving pain comprising the administration of such a compound to the patient.

Subgeneric to the compounds of formula I above are compounds of formula II below

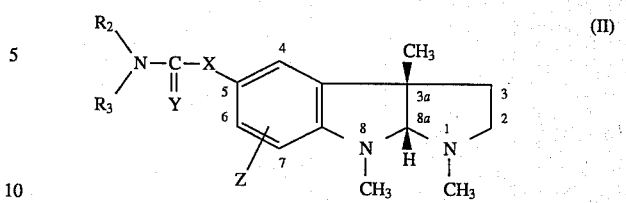

where X, Y, Z, $R_2$ and $R_3$ are as defined earlier with the proviso that when X and Y are both oxygen and Z and $R_3$ are both hydrogen, $R_2$ is not methyl or phenyl.

Also subgeneric to the compounds of formula I above are compounds of formula III below

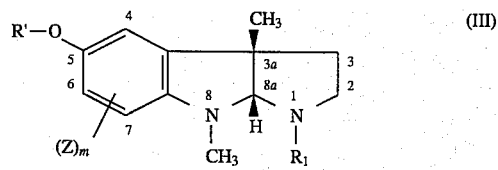

where $R_1$, Z and m are as defined earlier and R' is H, loweralkyl,

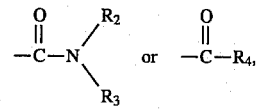

where $R_2$, $R_3$ and $R_4$ are as defined earlier with the proviso that when m is 1 and Z is hydrogen and $R_1$ is methyl, R' is not —$CONHCH_3$, —$CONHC_6H_5$, hydrogen, methyl or ethyl, and that when m is 1 and Z and $R_1$ are both hydrogen, R' is not hydrogen or methyl.

Unless otherwise stated or indicated, the following definitions shall apply throughout the specification and the appended claims.

The term alkyl shall mean a straight or branched alkyl group having from 1 to 22 carbon atoms. Examples of said alkyl include methyl, butyl, octyl, octadecyl etc.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term cycloalkyl shall mean a cycloalkyl group having from 3 to 8 carbon atoms. Said cycloalkyl group may be substituted with 1 or 2 loweralkyl groups, and it may also be substituted at one of the ring carbons so as to form a spiro compound each constituent ring of which being a cycloalkyl of 3 to 8 carbon atoms.

The term cycloalkenyl shall mean a cycloalkenyl group containing 3 to 8 carbon atoms and having only one double bond in the ring.

The term bicycloalkyl shall mean a bicycloalkyl group having from 7 to 11 carbon atoms.

The term halogen shall mean fluorine, chlorine, bromine or iodine.

The term aryl shall mean an unsubstituted phenyl group or naphthyl group, or a phenyl group substituted with 1, 2 or 3 substituent groups each of which being independently loweralkyl, halogen, nitro, loweralkoxy, hydroxy, or trifluoromethyl.

The term heteroaryl shall mean a group having the formula

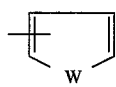

where W is O, S, NR$_5$ or CH=N, R$_5$ being hydrogen or loweralkyl and it shall include all the positional isomers. Thus, for instance, when W is S, the formula includes both 2-thienyl and 3-thienyl.

The compounds of this invention are prepared by utilizing one or more of the steps described below.

Throughout the description of the synthetic steps, the notations, X, R, R$_1$ through R$_5$, Y, Z and m shall have the respective meanings given above unless otherwise stated or indicated.

The heavy lines (◂) coming out of the 3a-carbon and 8a-carbon in formula I and other formulas presented in the specification and the appended claims signify that the substituents are above the average plane of the three-ring system. Thus, in formulas (I), (II) and (III), the substituents at the 3a- and 8a- carbons are cis inasmuch as they are on the same side of the three ring system. Where said substituents are both below the average plane of the three ring system, they are also cis. The first type of cis configuration will be referred to as 3aS-cis where both substituents are above the average plane of the ring and the second type will be referred to as 3aR-cis where both substituents are below the average plane of the ring. These two types of configuration are depicted below.

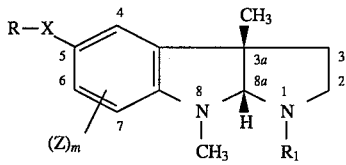

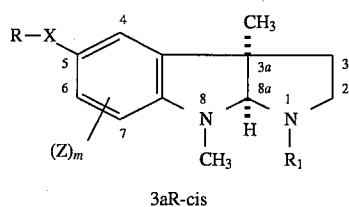

It is the intent of the present inventors to claim both of said cis compounds, namely, 3aS-cis compound and 3aR-cis compound for each structural formula, although only the former type is shown in the specification and the appended claims in order to save space. It is also the intent of the present inventors to claim all mixtures of the 3aS-cis and 3aR-cis compounds including the racemic mixture (1:1 ratio of 3aS-cis:3aR-cis).

STEP A

Starting with a compound of formula IV (where Z' is hydrogen, loweralkyl, halogen or nitro) and utilizing the synthetic scheme disclosed in Julian et al., J. Chem. Soc. 1935, 563–566 and 755–757, one can prepare compounds of the formulas VIII through XI. The synthetic scheme is outlined below, but for details the reader is referred to the original articles. For details of the optical resolution steps involved in the synthetic scheme, the reader is referred to Schonenberger et al., J. Med. Chem., 1986, Volume 29, 2268–2273; and Schonenberger et al., Helv. Chim. Acta, 1986, Volume 69, 283–287 and 1486–1497.

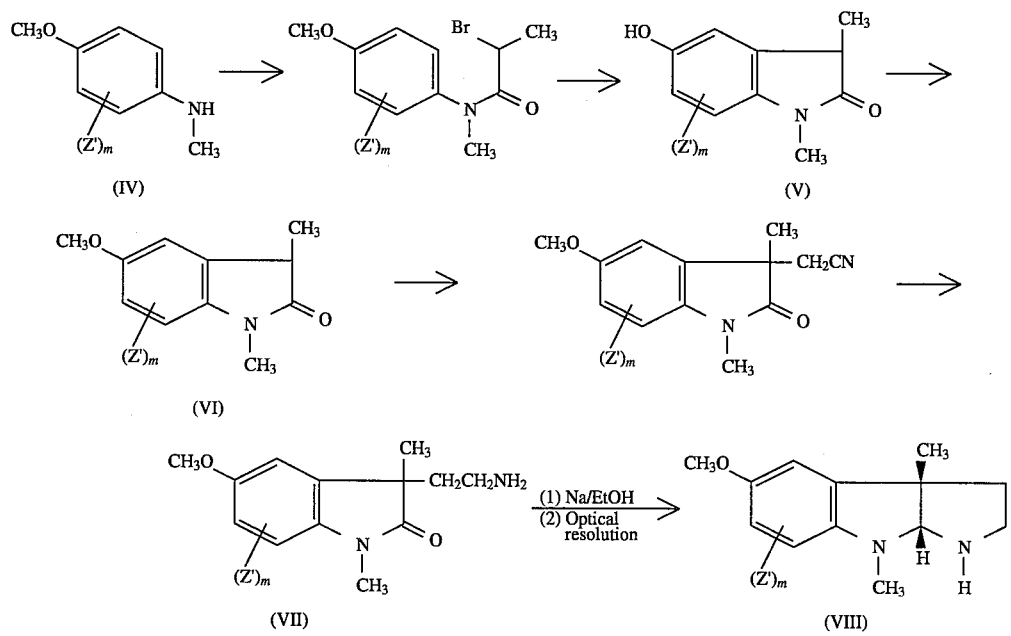

(1) C₆H₅CHO
(2) CH₃I
(3) hydrolysis
(4) Na/EtOH
(5) optical resolution

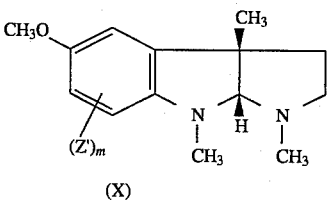

(X)

(Z' = H, loweralkyl, halogen or NO₂)

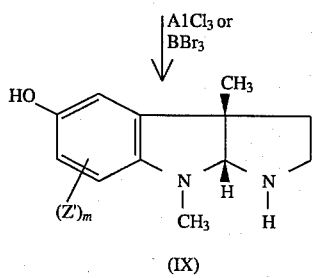

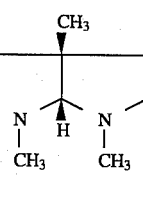

(XI)

STEP B

As an alternative to STEP A above, one can introduce Cl, Br or NO₂ into the $C_7$-position of compound Xa and obtain compound Xb depicted below (where Z is Cl, Br or NO₂) by reacting compound Xa with N-chlorosuccinimide, N-bromosuccinimide or NO₂BF₄, respectively, according to a routine procedure known in the art.

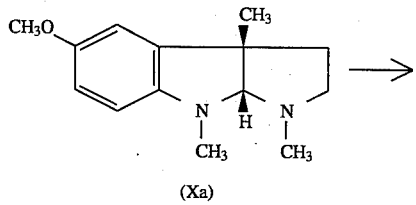

(Xa)

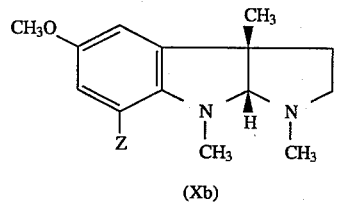

(Xb)

(Z = Cl, Br or NO₂)

STEP C

Compound XI can readily be converted to an ether compound of formula XII where R' is loweralkyl according to a routine method known in the art. Thus, for instance, when R' is ethyl, compound XI is reacted with ethyl p-toluenesulfonate to obtain the ethyl ether.

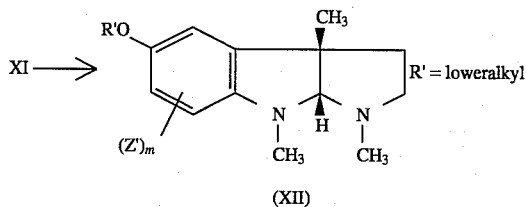

(XII)

Alternatively, the ether linkage may be introduced during the synthetic sequence described in STEP A above. Namely, the ether linkage may be introduced by reacting compound V with a suitable reagent according to a routine method known in the art.

STEP D

Compound XI is reacted with an isocyanate of the formula $R_2$—N=C=O to afford a compound of formula XIII below.

XI + R₂—N=C=O 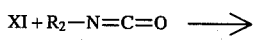

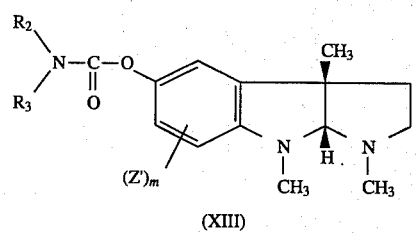

(XIII)

Typically, compound XI and the isocyanate are dissolved in a suitable solvent such as anhydrous tetrahydrofuran which has previously been degassed. Degassing is helpful because compound XI is susceptible to air oxidation. It is also helpful to add a catalytic amount (less than equivalent amount) of sodium metal to the resultant solution in order to facilitate the reaction. Said reaction is usually conducted between room temperature and about 70° C. Reflux condition is particularly convenient.

STEP E

A compound of formula XIV below (where $R_3$ is not hydrogen) is prepared by reacting compound XI with 1,1'-carbonyldiimidazole and thereafter adding a secondary amine of the formula

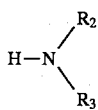

($R_3$ is not hydrogen) to the solution.

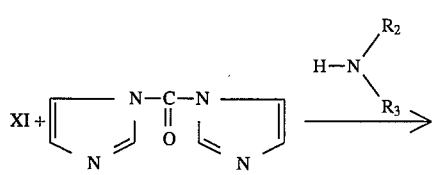

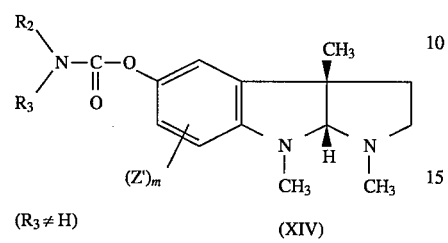

Said reaction between compound XI and 1,1'-carbonyldiimidazole is typically conducted by preparing a degassed solution of compound XI in a suitable solvent such as dichloromethane, adding 1,1'-carbonyldiimidazole to the solution and stirring the solution at room temperature for a suitable length of time such as one hour. Said carbamation reaction is typically conducted by adding the secondary amine

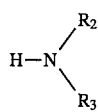

to the solution obtained above and stirring the solution at room temperature for a few hours.

As an alternative to the above reaction route, one can prepare compound XIV by reacting compound XI with a carbamyl chloride of the formula

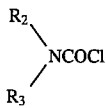

($R_3$ is not hydrogen) (typically in a degassed solution comprising the reactants, a suitable solvent such as anhydrous dimethylformamide and potassium carbonate, at room temperature), but the former method is much more preferable.

Although the substituent at the 1-position is a methyl group in the reaction depicted above, it will be apparent that said STEP E can be applied to other cases, namely, those where the substituent at the 1-position is loweralkyl, aryl-loweralkyl, heteroarylloweralkyl, cycloalkylmethyl or loweralkenylmethyl. The same is also true of STEP F described below.

STEP F

A compound of formula XV below (where $R_3$ is not hydrogen) is prepared by reacting compound XI with 1,1'-thiocarbonyldiimidazole and thereafter adding a secondary amine

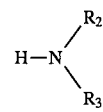

($R_3$ is not hydrogen) to the solution. This step is conducted in substantially the same manner as in STEP E described above.

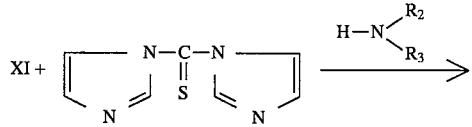

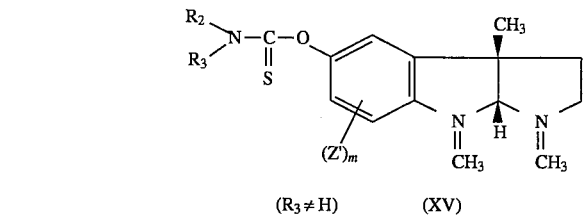

As an alternative to the above reaction route, one can prepare compound XV by reacting compound XI with a thiocarbamyl chloride of the formula

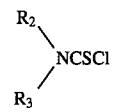

($R_3$ is not hydrogen) (typically in a degassed solution comprising the reactants, a suitable solvent such as anhydrous dimethylformamide and potassium carbonate, at room temperature), but the former method is much more preferable.

STEP G

Instead of relying on STEP A for the introduction of Br or $CH_3$ into the $C_6$-position of the ring system, one can, as a special case, introduce Br or $CH_3$ into the $C_6$-position of compound IIa and obtain compound IIb depicted below (where Z' is Br or $CH_3$) by use of the method described by Sibi and Snieckus, J. Org. Chem., 1983, Volume 48, 1935–1937. Thus, compound IIa is reacted with sec-BuLi and the resultant lithio compound (Li atom at the $C_6$-position) is reacted with bromine or methyl iodide to obtain compound IIb.

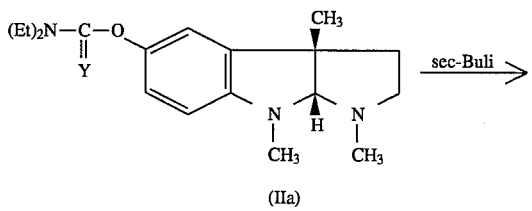

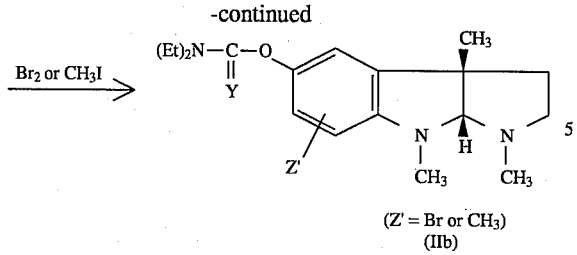

(Z' = Br or CH₃)
(IIb)

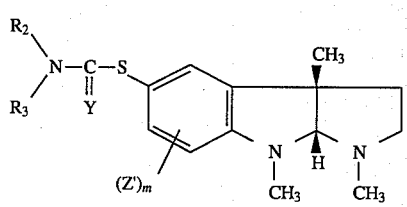

STEP K

A compound of formula XIX can be prepared by reacting a carboxylic acid or thiocarboxylic acid of the formula

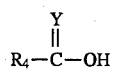

with 1,1'-carbonyldiimidazole and thereafter adding to the mixture a compound of formula XX obtained from one of the foregoing steps.

STEP H

A thiophenolic derivative of formula XVI can be prepared by heating a compound of formula XVa (where $R_3$ may be hydrogen) obtained in STEP F. This rearrangement reaction is typically conducted by heating said compound at an elevated temperature, some cases, of about 150° C. to 300° C. for a few hours.

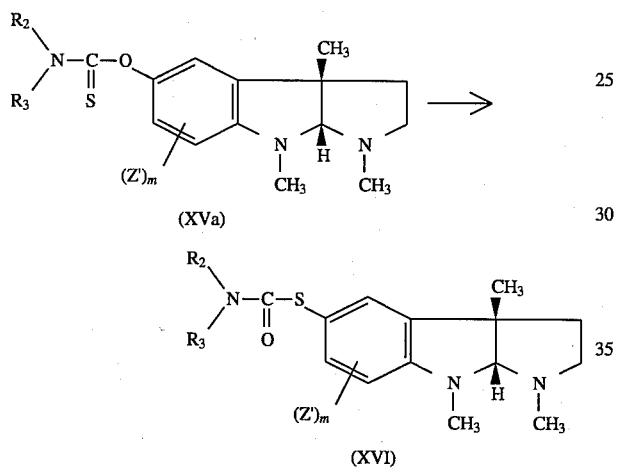

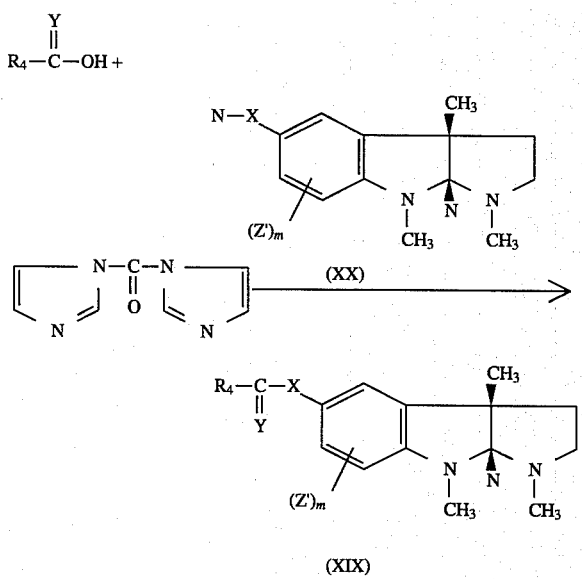

STEP I

A thiophenol compound of formula XVII can be prepared by hydrolyzing compound XVI. Said hydrolysis is typically conducted in a suitable degassed solvent such as ethanol containing sodium hydroxide and by stirring the reaction mixture at room temperature for a few hours.

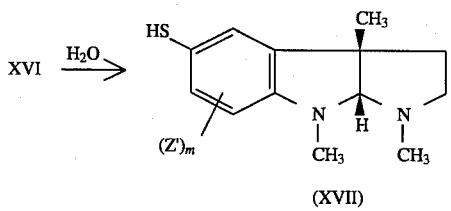

STEP J

Once compounds XVII are obtained, compounds of formula XVIII below can be obtained by utilizing STEPS D through G described above.

STEP L

In all the products obtained in STEPS B through K, the substituent on the 1-position of the ring is a methyl group. However, the corresponding compounds where said substituent is hydrogen can be obtained by first protecting the amino hydrogen with a suitable group, utilizing one or more of STEPS B through K and thereafter removing the protective group, or alternatively in certain cases by introducing a desired group —X—R or —(Z')ₘ during the synthetic sequence leading to compound VIII which is described in STEP A. In this manner, one can obtain compounds of formula XXI below.

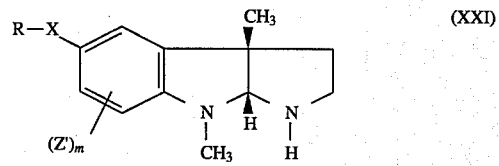

STEP M

A compound of formula XXII can be prepared by reacting a compound of formula XXI with a bromide compound of the formula $R_1Br$ where $R_1$ is not hydrogen in a routine manner known in the art.

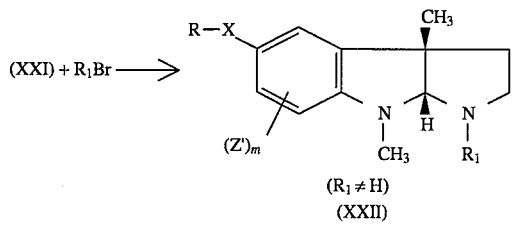

(XXI) + $R_1Br$ ⟶ (XXII)

($R_1 \neq H$)

STEP N

A compound of formula I where one or both of the groups $(Z)_m$ are —$NH_2$ can be prepared by reducing the corresponding nitro compound of formula I where one or both of the groups $(Z)_m$ are —$NO_2$ according to a routine manner known to the art.

STEP O

A compound of formula I where one or both of the groups $(Z)_m$ are loweralkylcarbonylamino, arylcarbonylamino, loweralkoxycarbonylamino or loweralkylamino can be prepared by reacting the corresponding amino compound of formula I where one or both of the groups $(Z)_m$ are —$NH_2$ with a suitable acylating agent or alkylating agent according to a routine manner known in the art.

The compounds of formula I of the present invention are useful in the treatment of various memory dysfunctions characterized by decreased cholinergic function, such as Alzheimer's disease.

This utility is manifested by the ability of these compounds to inhibit the enzyme acetylcholtnesterase and thereby increase acetylcholine levels in the brain.

Cholinesterase Inhibition Assay

Cholinesterases are found throughout the body, both in brain and in serum. However, only brain acetylcholinesterase (ACHE) distribution is correlated with central cholinergic innervation. This same innervation is suggested to be weakened in Alzheimer patients. Therefore, specific inhibitors of brain AChE (as opposed to serum ACHE) will give rise to fewer side effects and thus lower toxicity than physostigimine (an unspecific AChE inhibitor). We have determined in vitro inhibition of acetylcholinesterase activity in rat striatum and in vitro inhibition of butrylcholinesterase activity in human serum according to the methods described below. Results of some of the compounds of this invention as well as those of physostigmine are presented in Table 1.

In Vitro Inhibition of Acetylcholinesterase Activity in Rat Striatum

Acetylcholinesterase (ACHE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying cholinesterase activity. This is a modification of the method of Ellman et al., Biochem. pharmacol. 7, 88 (1961).

Procedure

A. Reagents 1. 0.05M Phosphate buffer, pH 7.2
   a) 6.85 g $NaH_2PO_4 \cdot H_2O$/100 ml distilled $H_2O$
   b) 13.40 g $Na_2HPO_4 \cdot 7H_2O$/100 ml distilled $H_2O$
   c) add a) to b) until pH reaches 7.2
   d) Dilute 1:10

2. Chromogen-substrate buffer
   a) 9.9 mg 5,5-dithtobisnitrobenzoic acid (DTNB) (0.25 mM)
   b) 99 mg s-acetylthiocholine chloride (5 mM)
   c) q.s. to 100 ml with 0.05M phosphate buffer, pH 7.2 (reagent 1)

3. For most assays, a 2 mM stock solution of the test drug is made up in a suitable solvent and serially diluted such that the final concentration in the preincubation step ranges from $10^{-3}$ to $10^{-6}$M. Different concentrations may be used depending on the potency of the drug.

Tissue Preparation

Male wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 50 microliter aliquot of the homogenate is added to 50 microliter vehicle of various concentrations of the test drug and preincubated for 10 minutes at room temperature.

C. Assay

1. For routine $IC_{50}$ determinations the Abbott Bichromatic Analyzer, ABA-100, is used to determine acetylcholinesterase activity.
   Instrument settings
   Filter: 450–415
   Incubation temperature: 30° C.
   Decimal point: 0000.
   Analysis time: 5 minutes
   Carousel Revolution: 3
   Reaction direction: down :endpoint
   Syringe plate : 1:101 dilution
   Following the 10 minute preincubation of the tissue (enzyme) with the inhibitor, the samples are mixed with the substrate chromogen buffer by the ABA-100. Using the indicated instrument settings the ABA-100 automatically reads the color reaction and prints out the results in enzyme units after 15 minutes.

2. The enzyme activity can also be measured with Gilford 250 spectrophotometer. This method is used for more accurate kinetic measurments.
   Instrument settings
   Lamp: visible Filter: no filter
Wavelength: 412 nm
Slit width: 0.2 mm
Selection: small aperture
Calibrated absorbance: 1.0 unit full scale
Chart speed: 0.5 cm/min
Reagents are added to the reference and sample side of a split curvette as follows.

| Reference | Sample |
|---|---|
| 0.8 ml 0.05M phosphate buffer | 0.8 ml 0.05M phosphate buffer |
| 0.8 ml Chromogen-substrate buffer | 0.8 ml Chromogen-substrate buffer |
|  | 10 microliter enzyme (tissue homogentate) |

The uninhibited activity of the enzyme (tissue homogenate) is first determined. Test drugs are made up in a suitable solvent and added in suitable dilutions to the buffer vehicle. The reaction rate is determined by the slope of the recorded absorbance change. The actual rate (moles/liter/rain) can be calculated as described in the following formula rate (moles/liter/min)=slope/($1.36 \times 10^4$)

In Vitro Inhibition of Butyrylcholinesterase Activity in Human Serum

This assay can be used in conjunction with the acetylcholinesterase assay to determine the enzyme selectivity of various cholinesterase inhibitors.

Butyrylcholinesterase (BChE), which is sometimes called pseudocholinesterase, preferentially hydrolyzes butyrylcholine. This enzyme is found in the highest amounts in serum, but its physiological role is not known. Ethopropazine and tetraisopropyl pyrophosphoramide (ISO-OMPA) are selective inhibitors of butyrylcholinesterase. An ex vivo experiment with ISO-OMPA has shown that inhibition of butyrylcholinesterase is not correlated with any significant acute cholinomimetic effects.

Procedure

A. Reagents 1. 0.05M Phosphate buffer, pH 7.2
   a) 6.85 g $NaH_2PO_4 \cdot H_2O$/100 ml distilled $H_2O$
   b) 13.40 g $Na_2HPO_4 \cdot H_2O$/100 ml distilled $H_2O$
   c) Add (a) to (b) until pH reaches 7.2
   d) Dilute 1:10

2. Chromogen-substrate buffer
   a) 9.9 mg 5,5-dithiobisnitrobenzoic acid (DTND)
   b) 113 mg s-butyrylthiocholine chloride
   c) q.s. to 100 ml with 0.05M phosphate buffer, pH 7.2 (reagent 1).
   The resulting substrate concentration is 5 mM and DTNB is 0.25 mM.

3. For most assays a 1.1 mM stock solution is made up in suitable solvent and serially diluted, such that the final concentration in the preincubation step ranges from $10^{-3}$ to $10^{-6}$M. Different concentrations may be used depending on the potency of the test drug.

B. Enzyme Preparation

A vial of lyophilized human serum (Precilip, Biodynamics, Houston, Tex.) is reconstituted in 3 ml of distilled water. A 10 microliter aliquot of this suspension is added to 90 microliter of the vehicle or various concentrations of the test drug and preincubated for 10 minutes, at room temperature.

C. Assay

Substantially the same procedure is used as described above in Section C of the Procedure used for determining the inhibition of acetylcholinsterase activity.

TABLE 1

| Compound | Inhibitory Concentration ($10^{-6}$M) | |
|---|---|---|
|  | Brain AChE | Serum AChE |
| Physostigmine (namely, (3aS-cis)-1,2,3,3a,8,8a-hexahydro-1,3a,8-trimethyl-pyrrolo[2,3-b]indol-5-ol, methyl carbamate) | 0.1 | 0.06 |
| (3aS-cis)-1,2,3,3a,8,8a-hexahydro-1,3a,8-trimethyl-pyrrolo[2,3-b]indol-5-ol, cyclohexyl carbamate | 0.9 | >1000 |
| [3aS-[3aα,5 (R*), 8aα]]-1,2,3,3a,8,8a-hexahydro-1,3a,8-trimethylpyrrolo-[2,3-b]indol-5-ol, (1-phenyl)ethyl carbamate | 3.1 | >1000 |
| [3aS-[3aα,5(S*),8aα]]-1,2,3,3a,8,8a-hexahydro-1,3a,8-trimethylpyrrolo-[2,3-b]indol-5-ol, (1-phenyl)ethyl carbamate | 1.2 | 0.9 |
| (3aS-cis)-1,2,3,3a,8,8a-hexahydro-1,3a,8-trimethyl-pyrrolo[2,3-b]indol-5-ol, 3-chlorophenyl carbamate | 0.6 | >1000 |

This utility is further demonstrated by the ability of these compounds to restore cholinergically deficient memory in the Dark Avoidance Assay, where they are generally active over a broader dose range than heretofore known compounds, a distinct therapeutic advantage.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is countered by an active test compound, resulting in a greater interval before re-entry into the dark compartment.

The results for active compound are expressed as the percent of a group of animals in which the effect of scopolamine is countered, as manifested by an increased interval between being placed in the test chamber and re-entering the dark compartment.

The results of some of the compounds of this invention are presented in Table 2 along with the result for physostigmine.

TABLE 2

| Compound | Dose mg/kg Body Weight | % of Animals With Scopolamine Induced Memory Deficit Reversed |
|---|---|---|
| Physostigmine (namely, (3aS-cis)-1,2,3,3a,8,8a-hexahydro-1,3a,8-trimethyl-pyrrolo[2,3-b]indol-5-ol, methyl carbamate) | 0.31 | 20% |
| (3aS-cis)-1,2,3,3a,8,8a-hexahydro-1,3a,8-trimethyl-pyrrolo[2,3-b]indol-5-ol, cyclohexyl carbamate | 0.16 | 31% |
| [3aS-[3aα,5(R*),8aα]]-1,2,3,3a,8,8a-hexahydro-1,3a,8-trimethylpyrrolo-[2,3-b]indol-5-ol, (1-phenyl)ethyl carbamate | 0.31 | 20% |
| [3aS-[3aα,5(S*),8aα]]-1,2,3,3a,8,8a-hexahydro-1,3a,8-trimethylpyrrolo-[2,3-b]indol-5-ol, (1-phenyl)ethyl carbamate | 1.25 | 67% |
| (3aS-cis)-1,2,3,3a,8,8a-hexahydro-1,3a,8-trimethyl-pyrrolo[2,3-b]indol-5-ol, (4-pyridinyl) carbamate | 0.31 | 27% |
| (3aS-cis)-1,2,3,3a,8,8a-hexahydro-1,3a,8-trimethyl-pyrrolo[2,3-b]indol-5-ol, 3-chlorophenyl carbamate | 5.0 | 20% |

Additionally, some of the compounds of this invention exhibit antidepressant activities, which activities being particularly helpful for patients suffering from Alzheimer's disease. The antidepressant activities were evaluated in this invention on the basis of prevention of tetrabenazine-induced ptosis in mice, yohimbine toxicity potentiation and inhibition of $^3$H-norepinephrine uptake. The test methods and results are described below.

Prevention of Tetrabenazine-Induced Ptosis in Mice

Tetrabenazine (TBZ) induces behavioral depression with concomitant ptosis in mice similar to reserpine. Antidepressant compounds, both monoamineoxidase inhibitors and tricyclics, are known to prevent or antagonize these effects and the degree of antagonism correlates with clinical efficacy. The prevention of TBZ-induced ptosis in mice is used as a preliminary screen for possible antidepressant activity. The method used in this invention is as follows:

Male mice weighing 20 to 30 grams are used in test groups of five subjects. All compounds are dissolved or suspended with a suitable surfactant in distilled water and administered in volumes of 10 ml/kg of body weight. TBZ solution is made from the methanesulfonate salt and the concentration is adjusted to enable administration of 60 mg/kg of base by intraperitoneal (i.p.) injection.

The pretreatment time is measured from the time of dosing to observation. Therefore, when a 30-minute pretreat is utilized, drug and TBZ are given simultaneously. A control group receives solvent and TBZ at intervals identical to drug group. For a primary screen, the drug is administered i.p. and a group size of five is utilized. Eight animals/group are used for a dose range.

Thirty minutes after TBZ, the subjects are placed in individual plastic containers (10.5×8×6 inches) in the presence of white noise and one minute after the transfer, they are scored for ptosis on the following scale: Eyes closed=4, eyes ¾ closed=3, eyes½ closed=2, eyes ¼ closed=1, eyes open=0. The total score for each group of five in a primary screen will, therefore, be from 0 to 20 and these scores are used as indications of drug activity.

The vehicle control group score is used as a determinant of the validity of each test. If the control score is less than 17, the results are discarded and the test repeated. The calculation of percent inhibition of ptosis is:

$$\frac{\text{(Control Score} - \text{Drug Score)}}{\text{Control score}} \times 100\%$$

For $ED_{50}$ estimation, four or five doses are administered in order to bracket the estimated value and only vehicle control scores of 27 to 32 are accepted to assure the accuracy of the $ED_{50}$ estimation.

Linear regression analysis is used to estimate $ED_{50}$ values and 95% confidence intervals.

The results of some of the compounds of this invention are shown in Table 3.

Yohimbine Toxicity Potentiation

The potentiation of yohimbine toxicity is considered an additional test for screening antidepressant drugs. The method used in this invention is as follows:

Male mice weighing 20 to 30 grams are used. They are housed under standard laboratory conditions with free access to food and water. Compounds are dissolved in distilled water and a suitable surfactant is added in case of poor solubility. Yohimbine hydrochloride is dissolved in distilled water as well. Both compound and yohimbine are adminstered in a volume of 10 mg/kg.

Compounds and vehicle are administered orally 60 minutes prior to a sublethal dose (30 mg/kd s.c.) of yohimbine hydrochloride which alone causes death in about 1% of mice (4 out of 400). Ten mice per group are then placed in plastic cages (26×10×16 cm) with food and water available ad libitum. Mortality rate is assessed 18 hours postdosing. $ED_{50}$ is defined as dose of drug causing death in 5/10 mice and is calculated by probit analysis. The results of some of the compounds of this invention are presented in Table 3.

TABLE 3

| Compound | % inhibition @ dose (mg/kg) | |
|---|---|---|
| | TBZ | YTP |
| (3aS-cis)-1,2,3,3a,8,8a-hexahydro-1,3a,8-trimethyl-pyrrolo[2,3-b]indol-5-ol, cyclohexyl carbamate | 20% @ 1.25 | — |
| [3aS-[3aα,5 (R*),8aα]]-1,2,3,3a,8,8a-hexahydro-1,3a,8-trimethylpyrrolo-[2,3-b]indol-5-ol, (1-phenyl)ethyl carbamate | 35% @ 20 | 90% @ 40 |
| [3aS-[3aα,5 (S*),8aα]]-1,2,3,3a,8,8a-hexahydro-1,3a,8-trimethylpyrrolo-[2 3-b]indol-5-ol, (1-phenyl)ethyl carbamate | 50% @ 20 | — |
| (3aS-cis)-1,2,3,3a,8,8a-hexahydro-1,3a,8-trimethyl-pyrrolo[2,3-b]indol-5-ol, 3-chlorophenyl carbamate | 31% @ 80 | 63% @ 80 |

$^3$H-Norepinephrine Uptake in Rat Whole Brain or Hypothalamic Synaptosomes

This assay is used as a biochemical screen for potential antidepressants which block norepinephrine uptake.

The neuronal re-uptake mechanism for norepinephrine (NE) is the most important physiological means for inactivating NE by removing the transmitter from the synaptic cleft. NE uptake is accomplished by a saturable, stereospecific, high-affinity ($K_m=10^{-7}-10^{-6}$M), sodium-dependent, active transport system, which has been shown to exist in both peripheral and central nervous system tissues, using slice, homogenate and purified synaptosome preparations. NE uptake is potently inhibited by cocaine, phenethylamines and tricyclic antidepressants. It is also inhibited by ouabain, metabolic inhibitors and phenoxybenzamine. The inhibition of NE uptake by clinically effective tricyclic antidepresasnts is an important link in the catecholamine hypothesis of affective disorders.

There are large regional variations in NE uptake which correlate with the endogenous levels of ME. The hypothalamus shows the highest level of NE and the greatest uptake. This region is used for further testing of compounds showing activity in whole brain preparations.

Synaptosomal $^3$H-NE uptake is a useful marker for the integrity of noradrenergic neurons, after lesioning experiments, as well as an assay for compounds which potentiate the action of NE by blocking the reuptake mechanism.

Procedure

A. Animals: Male CR Wistar rats (100–125 g)
B. Reagents
1. Krebs-Henseleit Bicarbonate Buffer, pH 7.4 (KHBB) Make a 1 liter batch, containing the following salts.

|  | grams/L | mM |
| --- | --- | --- |
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |
| Prior to use add: |  |  |
| Dextrose | 2 mg/ml | 11.1 |
| Iproniazid phosphate | 0.30 mg/ml | 0.1 |

Aerate for 60 min. with 95% O$_2$/5% CO$_2$, check pH (7.4±0.1).

2. 0.32M Sucrose: 21.9 g of sucrose, q.s. to 200 ml.

3. L(−)-Norepinephrine bitartrate is procured form a commercial source. A 0.1 mM stock solution is made up in 0.01N HCl. This is used to dilute the specific activity of the radiolabeled NE.

4. Levo-[Ring-2,5,6-$^3$H]-Norepinephrine (40–50 Ci/mmol) is obtained from a commercial course.
The final desired concentration of 3H-NE in the assay is 50 nM. The dilution factor is 0.8; therefore the KHBB is made up to contain 62.5 nM [$^3$H]-NE. Add to 100 ml of KHBB:

| A. 59.4 microliter of 0.1 mM NE = | 59.4 nM |
| --- | --- |
| B. 0.31 nmole of $^3$H-NE = | 3.1 nM |
|  | 62.5 nM |

5. For most asays, a 1 mM stock solution of the test compound is made up in a suitable solvent and serially diluted such that the final concentration in the assay ranges from $2\times10^{-8}$ to $2\times10^{-5}$M. Seven concentrations are used for each assay. Higher or lower concentrations may be used depending on the potency of the test compound.

C. Tissue Preparation

Male Wister rats are decapitated and brains rapidly removed. Either whole brain minus cerebella or hypothalamus is weighed and homogenized in 9 volumes of ice-cold 0.32M sucrose using a Potter-Elvejhem homogenizer. Homogenization should be done with 4–5 up and down strokes at medium speeds to minimize synaptosome lysis. The homogenate is centrifuged at 1000 g for 10 min at 0°–4° C. The supernatant (S$_1$) is decanted and is used for uptake experiments.

D. Assay 800 microliter KHBB containing [$^3$H]-NE 20 microliter Vehicle or appropriate drug concentration 200 microliter Tissue suspension Tubes are incubated at 37° C. under a 95% O$_2$/5% CO$_2$ atmosphere for 5 minutes. For each assay, 3 tubes are incubated with 20 microliter of vehicle at 0° C. in an ice bath. After incubation all tubes are immediately centrifuged at 4000 g for 10 minutes. The supernatant fluid is aspirated and the pellets dissolved by adding 1 ml of a solubilizer. The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. IC$_{50}$ values are devied from log-probit analysis.

The results of some of the compounds of this invention are presented in Table 4 along with the result for physostigmine.

TABLE 4

| Compound | Reuptake Inhibition ($10^{-6}$M) of neurotransmitters Norepinephrine |
| --- | --- |
| Physostigmine (namely, (3aS-cis)-1,2,3,3a,8,8a-hexahydro-1,3a,8-trimethyl-pyrrolo[2,3-b]indol-5-ol, methyl carbamate) | >20 |
| (3aS-cis)-1,2,3,3a,8,8a-hexahydro-1,3a,8-trimethyl-pyrrolo[2,3-b]indol-5-ol, cyclohexyl carbamate | >20 |
| [3aS-[3aα,5 (R*), 8aα]]-1,2,3,3a,8,8a-hexahydro-1,3a,8-trimethylpyrrolo-[2,3-b]indol-5-ol, (1-phenyl)ethyl carbamate | 2.2 |
| [3aS-[3aα,5 (S*), 8aα]]-1,2,3,3a,8,8a-hexahydro-1,3a,8-trimethylpyrrolo-[2 3-b]indol-5-ol, (1-phenyl)ethyl carbamate | 12 |
| (3aS-cis)-1,2,3,3a,8,8a-hexahydro-1,3a,8-trimethyl-pyrrolo[2,3-b]indol-5-ol (4-pyridinyl) carbamate | >20 |
| (3aS-cis)-1,2,3,3a,8,8a-hexahydro-1,3a,8-trimethyl-pyrrolo[2,3-b]indol-5-ol, 3-chlorophenyl carbamate | 1.8 |

Furthermore, the compounds of this invention are in general less toxic than heretofore known compounds such as tacrine and physostigmine, making them therapeutically more acceptable.

LD$_{50}$ is determined by the dose (mg/kg) at which 50% of the test animals die within 24 hours. In many cases this dose is an approximation. The results of some of the compounds of this invention are presented in Table 5 along with the result for physostigmine.

TABLE 5

| Compound | LD$_{50}$ (mg/kg, i.p.) |
| --- | --- |
| Physostigmine (namely, (3aS-cis)-1,2,3,3a,8,8a-hexahydro-1,3a,8-trimethylpyrrolo[2,3-b]indol-5-ol, methyl carbamate) | ≅3 |
| (3aS-cis)-1,2,3,3a,8,8a-hexahydro-1,3a,8-trimethylpyrrolo[2,3-b]indol-5-ol, cyclohexyl carbamate | >5 <10 |
| [3aS-[3aα,5(R*),8aα]]-1,2,3,3a,8,8a-hexahydro-1,3a,8-trimethylpyrrolo[2 3-b]indol-5-ol, (1-phenyl) ethyl carbamate | >40 <80 |
| [3aS-[3aα,5(S*),8aα]]-1,2,3,3a,8,8a-hexahydro-1,3a,8-trimethylpyrrolo-[2,3-b]indol-5-ol, (1-phenyl)ethyl carbamate | ≅40 |
| (3aS-cis)-1,2,3,3a,8,8a-hexahydro-1,3a,8,-trimethylpyrrolo[2,3-b]-indol-5-ol, 4-pyridinyl carbamate | ≅40 |
| (3aS-cis)-1,2,3,3a,8,8a-hexahydro-1,3a,8-trimethylpyrrolo[2,3-b]-indol-5-ol, 3-chlorophenyl carbamate | >80 |

Compounds I of the present invention are also useful as analagesic agents due to their ability to alleviate pain in mammals. The activity of the compounds is demonstrated in the 2-phenyl-1,4-benzoquinone-induced writing (PQW) test in mice, a standard assay for analgesia [proc. Soc. Exptl. Biol. Med., 95, 729 (1957)] and in modified Halfher's analgesia.

The latter assay is used to evaluate analgesic activity by measuring drug-induced changes in the sensitivity of mice to pressure stress by placing an artery clip (2½ inches long) on their tail. The procedure used is a modification of the test developed by Halfnet, Dtsch. Med. Wschr. 55, 731 (1929), and it is described below.

METHOD

Male mice (Charles River, CD-1) from 18–30 grams are used for the test. An artery clip is applied to the root of the tail of a mouse (approximately ½ inch from the body) to induce pain. The animal quickly responds to this noxious stimuli by biting the clip or the location of the clip. This reaction time, the interval between stimulus onset and response, is recorded in 1/10-second increments by a stop watch.

For a time response, the screening dose (25 mg/kg) is administered subcutaneously (10 ml/kg) to the animal receiving food and water ad libitum before testing. Animals receiving the compound orally are fasted 18–24 hours before drug administration. Drug to be tested is prepared with distilled water and if insoluble, one drop of a surfactant is added.

Twenty-eight animals (seven/group) are administered the drug 15, 30, 45 and 60 minutes prior to testing.

The cut-off time (CO) is determined by taking the $\overline{x}$ average+(3) standard (SD) deviation of the combined response latencies of the control mice in all time periods.

Listed in Table 6 are test results of the analgesic activities of a compound of this invention along with those of eseroline salicylate used as a reference compound. As compared with eseroline, the compounds of this invention are much less toxic, have a longer lasting analgesic effect, have less physical dependence liability and are more stable.

$CO = \overline{x} + 3\ SD$ (seconds)

Any reaction time, in subsequent drug tests, which is greater than the CO (for the same time period) therefore exceeds 99% of a normal Gaussian distribution and is called "positive reponse" indicative of analgesic activity. A time response indicates the period of greatest analgesic effect after dosing. The ED$_{50}$ is determined at the peak time of drug activity. A minimum of three dose groups are used. ED$_{50}$'s are calculated using computer analysis.

TABLE 6

| | ANALGESIC ACTIVITY (ED$_{50}$) | |
| --- | --- | --- |
| Compound | PQW | Modified Haffner's Analgesia |
| 7-bromo-(3aS-cis)-1,2,3,3a,8,8a-hexahydro-1,3a,8-trimethylpyrrolo-[2,3-b]indol-5-ol | 0.041 mg/kg, sc 0.36 mg/kg, po | 0.55 mg/kg, sc |
| 7-bromo-(3aS-cis)-1,2,3,3a,8,8a-hexahydro-1,3a,8-trimethylpyrrolo-[2,3-b]indol-5-ol trimethylacetate hydrochloride | 0.8 mg/kg, sc | 0.6 mg/kg, sc |
| eseroline salicylate (reference compound) | 0.52 mg/kg, sc | 0.18 mg/kg, sc |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, salicylic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; and excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compounds, but may be varied depending upon the particular form and may conveniently be between 4% and about 70% of the weight of the unit. The amount of active compound in such compositions is such that a suitable dosage will be obtained. Preferred compositions and preparations according to the present invention are prepared so that a parenteral dosage unit contains between 0.5 to 100 milligrams of active compounds.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of the invention include those listed below as well as the 3aR-cis isomers thereof and mixtures of the 3aS-cis and 3aR-cis isomers including the racemic mixtures:

(3aS-cis)-1,2,3,3a,8,8a-hexahydro-1,3a,8-trimethyl-pyrrolo[2,3-b]indol-5-ol, octadecyl carbamate ester;

7-chloro-(3aS-cis)-1,2,3,3a,8,8a-hexahydro-1,3a,8-trimethyl-pyrrolo[2,3-b]indol-5-ol, methyl carbamate ester;

7-bromo-(3aS-cis)-1,2,3,3a,8,8a-hexahydro-1,3a,8-trimethyl-pyrrolo[2,3-b]indol-5-ol, methyl carbamate ester;

(3aS-cis)-1,2,3,3a,8,8a-hexahydro-1,3a,8-trimethyl-pyrrolo[2,3-b]indol-5-ol, N,N-diethyl carbamate ester;

(3aS-cis)-1,2,3,3a,8,8a-hexahydro-1,3a,8-trimethyl-pyrrolo[2,3-b]indol-5-ol, cyclopentylmethyl carbamate ester;

(3aS-cis)-1,2,3,3a,8,8a-hexahydro-1,3a,8-trimethyl-pyrrolo[2,3-b]indol-5-ol, (thien-3-yl)methyl carbamate ester;

(3aS-cis)-1,2,3,3a,8,8a-hexahydro-1,3a,8-trimethyl-pyrrolo[2,3-b]indol-5-ol, benzyl carbamate ester;

(3aS-cis)-1,2,3,3a,8,8a-hexahydro-1,3a,8-trimethyl-pyrrolo[2,3-b]indol-5-ol, (2-phenyl)ethyl carbamate ester;

[3aS-[3aα,5(R*),8aα]]-1,2,3,3a,8,8a-hexahydro-1,3a,8-trimethyl-pyrrolo[2,3-b]indol-5-ol, (1-phenyl)ethyl carbamate ester;

[3aS-[3aα,5(S*),8aα]]-1,2,3,3a,8,8a-hexahydro-1,3a,8-trimethylpyrrolo[2,3-b]indol-5-ol, (1-phenyl) ethyl carbamate ester;

7-chloro-[3aα,5 (R*),8aα]-1,2,3,3a,8,8a-hexahydro-1,3a,8-trimethyl-pyrrolo[2,3-b]indol-5-ol, (1-phenyl) ethyl carbamate ester;

7-bromo-[3aα,5(R*),8aδ]-1,2,3,3a,8,8a-hexahydro-1,3a,8-trimethyl-pyrrolo[2,3-b]indol-5-ol, (1-phenyl) ethyl carbamate;

(3aS-cis)-1,2,3,3a,8,8a-hexahydro-1,3a,8-trimethyl-pyrrolo[2,3-b]indol-5-ol, [1-(1-naphthyl)ethyl]carbamate ester;

(3aS-cis)-1,2,3,3a,8,8a-hexahydro-1,3a,8-trimethyl-pyrrolo[2,3-b]indol-5-ol, cyclohexyl carbamate ester;

7-chloro-(3aS-cis)-1,2,3,3a,8,8a-hexahydro-1,3a,8-trimethyl-pyrrolo[2,3-b]indol-5-ol, cyclohexyl carbamate ester;

7-bromo-(3aS-cis)-1,2,3,3a,8,8a-hexahydro-1,3a,8-trimethyl-pyrrolo[2,3-b]indol-5-ol, cyclohexyl carbamate ester;

(3aS-cis)-1,2,3,3a,8,8a-hexahydro-1,3a,8-trimethyl-pyrrolo[2,3-b]indol-5-ol, 4,4-dimethylcyclohexyl carbamate ester;

(3aS-cis)-1,2,3,3a,8,8a-hexahydro-1,3a,8-trimethyl-pyrrolo[2,3-b]indol-5-ol, 4-ethylcyclohexyl carbamate ester;

(3aS-cis)-1,2,3,3a,8,8a-hexahydro-1,3a,8-trimethyl-pyrrolo[2,3-b]indol-5-ol, spiro[5.5]undecan-3-yl carbamate ester;

(3aS-cis)-1,2,3,3a,8,8a-hexahydro-1,3a,8-trimethyl-pyrrolo[2,3-b]indol-5-ol cycloheptyl carbamate ester;

(3aS-cis)-1,2,3,3a,8,8a-hexahydro-1,3a,8-trimethyl-pyrrolo[2,3-b]indol-5-ol, 1,2-dimethylcyclohexen-4-yl carbamate ester;

(3aS-cis)-1,2,3,3a,8,8a-hexahydro-1,3a,8-trimethyl-pyrrolo[2,3-b]indol-5-ol, cyclohexen-1-yl carbamate ester;

(3aS-cis)-1,2,3,3a,8,8a-hexahydro-1,3a,8-trimethyl-pyrrolo[2,3-b]indol-5-ol, bicyclo[2.2.1]heptan-2-yl carbamate ester;

(3aS-cis)-1,2,3,3a,8,8a-hexahydro-1,3a,8-trimethyl-pyrrolo[2,3-b]indol-5-ol, 3-chlorophenyl carbamate ester;

(3aS-cis)-1,2,3,3a,8,8a-hexahydro-1,3a,8-trimethyl-pyrrolo[2,3-b]indol-5-ol, 4-chlorophenyl carbamate ester;

(3aS-cis)-1,2,3,3a,8,8a-hexahydro-1,3a,8-trimethyl-pyrrolo[2,3-b]indol-5-ol, 2,6-dimethylphenyl carbamate ester;

(3aS-cis)-1,2,3,3a,8,8a-hexahydro-1,3a,8-trimethyl-pyrrolo[2,3-b]indol-5-ol, 4-nitrophenyl carbamate ester;

(3aS-cis)-1,2,3,3a,8,8a-hexahydro-1,3a,8-trimethyl-pyrrolo[2,3-b]indol-5-ol, 4-pyridinyl carbamate ester;

(3aS-cis)-1,2,3,3a,8,8a-hexahydro-1,3a,8-trimethyl-pyrrolo[2,3-b]indol-5-ol, 4-methyl-piperazin-1-yl carbamate ester;

(3aS-cis)-1,2,3,3a,8,8a-hexahydro-1,3a,8-trimethyl-pyrrolo[2,3-b]indol-5-ol, 4-morpholinyl carbamate ester;

(3aS-cis)-1,2,3,3a,8,8a-hexahydro-1,3a,8-trimethyl-pyrrolo[2,3-b]indol-5-ol, 4-morpholinyl thiocarbamate ester;

(3aS-cis)-1,2,3,3a,8,8a-hexahydro-1,3a,8-trimethyl-pyrrolo[2,3-b]indol-5-ol, 2-(2,6-dichlorophenylimino)-1-imidazolidinyl carbamate ester;

(3aS-cis)-1,2,3,3a,8,8a-hexahydro-7-nitro-1,3a,8-trimethyl-pyrrolo[2,3-b]indol-5-ol, 3-chlorophenyl carbamate ester;

7-acetylamino-(3aS-cis)-1,2,3,3a,8,8a-hexahydro-1,3a,8-trimethyl-pyrrolo[2,3-b]indol-5-ol, 3-chlorophenyl carbamate ester;

6-bromo-(3aS-cis)-1,2,3,3a,8,8a-hexahydro-1,3a,8-trimethyl-pyrrolo[2,3-b]indol-5-ol, 3-chlorophenyl carbamate ester;

7-bromo-(3aS-cis)-1,2,3,3a,8,8a-hexahydro-1,3a,8-trimethyl-pyrrolo[2,3-b]indol-5-ol, n-heptyl carbamate ester;

[3aS-[3aα,5(S*),8aα(]-1,2,3,3a,8,8a-hexahydro-7-nitro-1,3a,8- trimethylpyrrolo[2,3-b]indol-5-ol, (1-phenyl)ethyl carbamate ester;

7-bromo-(3aS-cis)-1,2,3,3a,8,8a-hexahydro-5-methoxy-1,3a,8-trimethylpyrrolo[2,3-b]indole;

7-chloro-(3aS-cis)-1,2,3,3a,8,8a-hexahydro-5-methoxy-1,3a,8-trimethylpyrrolo[2,3-b]indole;

7-acetylamino-(3aS-cis)-1,2,3,3a,8,8a-hexahydro-5-methoxy-1,3a,8-trimethylpyrrolo[2,3-b]indole;

(3aS-cis)-1,2,3,3a,8,8a-hexahydro-5-methoxy-7-nitro-1,3a,8-trimethylpyrrolo[2,3-b]indole;

7-bromo-(3aS-cis)-1-cyclopropylmethyl-1,2,3,3a,8,8a-hexahydro-5-methoxy-3a,8-dimethylpyrrolo[2,3-b]indole;

7-bromo-(3aS-cis)-1,2,3,3a,8,8a-hexahydro-5-methoxy-1-(2-phenylethyl)-3a,8-dimethylpyrrolo[2,3-b]indole;

7-bromo-(3aS-cis)-1,2,3,3a,8,8a-hexahydro-5-methoxy-1-(2-propenyl)-3,8a-dimethylpyrrolo[2,3-b]indole;

7-bromo-1-(2-butenyl)-(3aS-cis)-1,2,3,3a,8,8a-hexahydro-5-methoxy-3,8a-dimethylpyrrolo[2,3-b]indole;

7-bromo-(3aS-cis)-1-cyclopropylmethyl-1,2,3,3a,8,8a-hexahydro-3a,8-dimethylpyrrolo[2,3-b]indol-5-ol;

7-bromo-(3aS-cis)-1,2,3,3a,8,8a-hexahydro-1-(2-phenylethyl)-8a,8-dimethylpyrrolo[2,3-b]indol-5-ol;

7-bromo-(3aS-cis)-1,2,3,3a,8,8a-hexahydro-1-(2-propenyl)-3a,8-dimethylpyrrolo[2,3-b]indol-5-ol;

7-bromo-1-(2-butenyl)-(3aS-cis)-1,2,3,3a,8,8a-hexahydro-3a,8-dimethylpyrrolo[2,3-b]indol-5-ol;

(3aS-cis)-1-cyclopropylmethyl-1,2,3,3a,8,8a-hexahydro-7-nitro-3a,8-dimethylpyrrolo[2,3-b]indol-5-ol;

(3aS-cis)-1,2,3,3a,8,8a-hexahydro-7-nitro-1-(2-propenyl)-3a,8-dimethylpyrrolo[2,3-b]indol-5-ol;

1-(2-butenyl)-(3aS-cis)-1,2,3,3a,8,8a-hexahydro-7-nitro-3a,8-dimethylpyrrolo[2,3-b]indol-5-ol;

(3aS-cis)-1,2,3,3a,8,8a-hexahydro-7-nitro-1-(2-phenylethyl)-3a,8-dimethylpyrrolo[2,3-b]indol-5-ol;

7-bromo-(3aS-cis)-1,2,3,3a,8,8a-hexahydro-1,3a,8-trimethylpyrrolo[2,3-b]indol-5-ol acetate;

(3aS-cis)-1,2,3,3a,8,8a-hexahydro-7-nitro-1,3a,8-trimethylpyrrolo[2,3-b]indol-5-ol acetate;

(3aS-cis)-1,2,3,3a-8,8a-hexahydro-7-nitro-1,3a,8-trimethylpyrrolo[2,3-b]indol-5-ol trimethylacetate;

7-bromo-(3aS-cis)-1,2,3,3a,8,8a-hexahydro-1,3a,8-trimethylpyrrolo[2,3-b]indol-5-ol heptanoate;

(3aS-cis)-1,2,3,3a,8,8a-hexahydro-7-nitro-1,3a,8-trimethylpyrrolo[2,3-b]indol-5-ol heptanoate; and 7-amino-(3aS-cis)-1,2,3,3a,8,8a-hexahydro-1,3a,8-trimethylpyrrolo[2,3-b]-5-ol, methyl carbamate ester.

The present invention will be described below in further detail with reference to the following examples.

EXAMPLE 1

(3aS-cis)-1,2,3,3a,8,8a-Hexahydro-1,3a,8-trimethyl-pyrrolo-[2,3-b]indol-5-ol, octadecyl carbamate ester A degassed solution containing octadecyl isocyanate (2.9 g) and eseroline (1.8 g) in 50 ml of dry tetrahydrofuran was treated with a catalytic chip of freshly cut sodium metal and thereafter stirred under a nitrogen blanket for 72 hours. The solution was then heated to reflux for 2 hours and thereafter evaporated. The residue was purified by flash chromatography (silica gel, 100:1 ethyl acetate/ethanol) to give 3.8 g of a wax. Recrystallization from ether gave 3.5 g of a white powder, mp 49–50°.

ANALYSIS: Calculated for $C_{32}H_{55}N_3O_2$: 74.80% C 10.79% H 8.17% N Found: 74.57% C 10.39% H 8.00% N

EXAMPLE 2

7-Chloro-(3aS-cis)-1,2,3,3a,8,8a-hexahydro-1,3a,8-trimethyl-pyrrolo[2,3-b]indol-5-ol, methyl carbamate ester A degassed solution of eserine (5.0 g) in 60 ml of methanol and 2 drops of concentrated hydrochloric acid was treated with N-chlorosuccinimide (2.6 g) in one portion with stirring. After 4 hours the solution was evaporated and the residue was purified by flash chromatography (silica gel, 4:1 ethyl acetate/methanol) to an oil. This oil was crystallized from hot ether to give 4.1 g of crystals, mp 129°–130° C.

ANALYSIS: Calculated for $C_{15}H_{20}ClN_3O_2$: 58.15% C 6.50% H 13.56% N Found: 58.18% C 6.54% H 13.59% N

EXAMPLE 3

7-Bromo-(3aS-cis)-1,2,3,3a,8,8a-hexahydro-1,3a,8-trimethyl-pyrrolo[2,3-b]indol-5-ol, methyl carbamate ester A degassed solution of eserine (2.0 g) in 50 ml of methanol and 2 drops of 48% HBr was treated with N-bromosuccinimide (1.4 g) in one portion. After 1 hour at room temperature, the solution was evaporated and the residue was purified by flash chromatography (silica gel, 4:1 ethyl acetate/methanol) to give an oil. This oil was crystallized from hot ether to give 1.6 g of crystals, mp 121°–122° C.

ANALYSIS: Calculated for $C_{15}H_{20}BrN_3O_2$: 50.85% C 5.69% H 11.86% N Found: 50.73% C 5.68% H 11.76% N

EXAMPLE 4

(3aS-cis)-1,2,3,3a,8,8a-Hexahydro-1,3a,8-trimethyl-pyrrolo-[2,3-b]indol-5-ol, N,N-diethyl carbamate ester A solution of eseroline (1.5 g) and diethylcarbamyl chloride (2.7 g) in 50 ml of dry dimethylformamide was degassed and thereafter treated with milled potassium carbonate (2.7 g). This slurry was stirred at room temperature for 5 hours and thereafter poured into 600 ml of water and extracted with 300 ml of ethyl acetate. The organic phase was washed with brine, dried over anhydrous magnesium sulfate, filtered and evaporated to a thick oil This oil was purified by flash chromatography (silica gel, 9:1 ethyl acetate/methanol) to an oil, which was crystallized from petroleum ether to give 1.7 g of crystals, mp 74°–76° C.

ANALYSIS: Calculated for $C_{18}H_{27}N_3O_2$: 68.10% C 8.57% H 13.23% N Found: 67.95% C 8.61% H 12.98% N

EXAMPLE 5

(3aS-cis)-1,2,3,3a,8,8a-Hexahydro-1,3a,8-trimethyl-pyrrolo[2,3-b]indol-5-ol, cyclopentylmethyl carbamate ester A degassed solution of eseroline (1.5 g) and cyclopentylmethyl isocyanate (1.2 g) in 70 ml of dry tetrahydrofuran was treated with a catalytic chip of sodium metal and heated under reflux for 3 hours. The solution was evaporated and the residue was purified by flash chromatography (silica gel, 4:1 ethyl acetate/methanol) to give a powder. This material was recrystallized from ether/petroleum ether to give 1.5 g of cubes, mp 105°–107° C.

ANALYSIS: Calculated for $C_{20}H_{29}N_3O_2$: 69.93% C 8.51% H 12.23% N Found: 70.17% C 8.70% H 12.30% N

EXAMPLE 6

(3aS-cis)-1,2,3,3a,8,8a-Hexahydro-1,3a,8-trimethyl-pyrrolo-[2,3-b]indol-5-ol, (thien-3-yl)methyl carbamate ester A degassed solution containing eseroline (1.5 g) and (thien-3-yl) methyl isocyanate (1.5 g) in 60 ml of dry tetrahydrofuran was treated with a catalytic chip of sodium metal and thereafter stirred at 60° for 6 hours. The solution was evaporated and the residue was purified by high performance liquid chromatography (HPLC) (silica gel, 16:3 ethyl acetate/methanol) to give 1.5 g of an oil. This oil slowly crystallized from ether to give 1.3 g of crystals.

ANALYSIS: Calculated for $C_{19}H_{23}N_3O_2S$: 63.85% C 6.48% H 11.75% N Found: 63.54% C 6.61% H 11.75% N

EXAMPLE 7

(3aS-cis)-1,2,3,3a,8,8a-Hexahydro-1,3a,8-trimethyl-pyrrolo[2,3-b]indol-5-ol, benzyl carbamate ester A solution of eseroline (1.7 g) and benzyl isocyanate (1.2 g) in 70 ml of degassed tetrahydrofuran was treated with catalytic chip of sodium metal and stirred at room temperature for 10 hours. The volatiles were removed and the residue was recrystallized from acetone/petroleum ether to give 2.1 of a powder, mp 167°–169° C.

ANALYSIS: Calculated for $C_{21}H_{25}N_3O_2$: 71.76% C 7.17% H 11.95% N Found: 71.55% C 6.97% H 11.95% N

EXAMPLE 8

(3aS-cis)-1,2,3,3a,8,8a-Hexahydro-1,3a,8-trimethyl-pyrrolo[2,3-b]indol-5-ol, (2-phenyl) ethyl carbamate ester A solution of eseroline (1.3 g) and phenylethyl isocyanate (1.03 g) in 50 ml of degassed tetrahydrofuran was treated with a catalytic chip of sodium metal. The solution was heated to reflux for 4 hours and thereafter evaporated. The residue was recrystallized from acetone/petroleum ether to give 1.7 g of needles, mp 152°–155° C.

ANALYSIS: Calculated for $C_{22}H_{27}N_3O_2$: 72.29% C 7.45% H 11.49% N Found: 72.33% C 7.49% H 11.56% N

EXAMPLE 9

[3aS-[3aα,5(R*),8aα]]-1,2,3,3a,8,8a-Hexahydro-1,3a,8-trimethyl-pyrrolo[2,3-b]indol-5-ol, (1-phenyl) ethyl carbamate ester A degassed solution containing eseroline (1.7 g) and S-(−)-α-methylbenzyl isocyanate (1.0 g) in 50 ml of dry tetrahydrofuran was treated with a catalytic chip of sodium metal and stirred at room temperature for 1 hour. This solution was heated under reflux for 5 hours and evaporated to a foam. This foam was purified by flash chromatography (alumina, ethyl acetate) and thereafter recrystallized from ether/petroleum ether to give 1.6 g of a powder, mp 113°–114° C.

ANALYSIS: Calculated for $C_{22}H_{27}N_3O_2$: 72.29% C 7.45% H 11.49% N Found: 72.37% C 7.68% H 11.37% N

EXAMPLE 10

[3aS-[3aα,5(S*),8aα]]-1,2,3,3a,8,8a-Hexahydro-1,3a,8-trimethyl-pyrrolo[2,3-b]indol-5-ol, (1-phenyl) ethyl carbamate ester A degassed solution containing eseroline (1.5 g) and R-(+)-methylbenzyl isocyanate (1.0 g) in 60 ml of dry tetrahydrofuran was treated with a catalytic chip of sodium metal and stirred at room temperature for 1 hour. This solution was heated to reflux for 5 hours and thereafter evaporated. The residue was purified by flash chromatography (alumina, ethyl acetate) to a powder. This powder was recrystallized from ether/petroleum ether to give 2.0 g of crystals, mp 151°–153° C.

ANALYSIS: Calculated for $C_{22}H_{27}N_3O_2$: 72.29% C 7.45% H 11.49% N Found: 72.10% C 7.63% H 11.36% N

EXAMPLE 11

7-Chloro-[3aα,5(R*),8aα]-1,2,3,3a,8,8a-hexahydro-1,3a,8-trimethyl-pyrrolo[2,3-b]indol-5-ol, (1-phenyl)ethyl carbamate ester A degassed solution containing 7-chloroeseroline (1.3 g) and S(−)—-methylbenzyl isocyanate (1.0 g) in 60 ml of dry tetrahydrofuran was treated with a catalytic chip of sodium metal and stirred at 50° for 3 hours. This solution was evaporated and the residue recrystallized twice from dichloromethane to give 1.4 g of crystals, mp 172°–173° C.

ANALYSIS: Calculated for $C_{22}H_{26}ClN_3O_2$: 66.07% C 6.55% H 10.50% N Found: 65.81% C 6.59% H 10.43% N

EXAMPLE 12

7-Bromo-[3aα,5(R*),8aα]-1,2,3,3a,8,8a-hexahydro-1,3a,8-trimethylpyrrolo[2,3-b]indol-5-ol, (1-phenyl) ethyl carbamate ester A degassed solution of 7-bromoeseroline (1.5 g) and (S)-(−)-α-methylbenzyl isocyanate (1.0 g) in 60 ml of dry tetrahydrofuran was treated with a catalytic chip of sodium metal and stirred at 60 for 4 hours. The resulting solution was evaporated and the remaining powder recrystallized twice from chloroform to give 1.4 g of crystals, mp 183°–185°.

ANALYSIS: Calculated for $C_{22}H_{26}BrN_3O_2$: 59.46% C 5.89% H 9.45% N Found: 59.10% C 5.80% H 9.33% N

EXAMPLE 13

(3aS-cis)-1,2,3,3a,8,8a-Hexahydro-1,3a,8-trimethyl-pyrrolo[2,3-b]indol-5-ol, [1-(1-naphthyl)ethyl]carbamate ester A solution containing eseroline (1.5 g) and racemic 1-(1-naphthyl) ethyl isocyanate (1.9 g) in 70 ml of dry tetrahydrofuran was degassed and treated with a catalytic chip of sodium metal. After 16 hours under reflux, the solution was evaporated and the residue was purified by flash chromatography (silica gel, 9:1 ethyl acetate/methanol) to give 1.9 g of a solid. This material was recrystallized from ether/petroleum ether to give 1.7 g of cubes, mp 147°–15° C.

ANALYSIS: Calculated for $C_{26}H_{29}N_3O_2$: 75.15% C 7.03% H 10.11% N Found: 75.15% C 7.09% H 10.04% N

EXAMPLE 14

(3aS-cis)-1,2,3,3a,8,8a-Hexahydro-1,3a,8-trimethyl-pyrrolo[2,3-b]indol-5-ol cyclohexyl carbamate ester A degassed solution containing eseroline (1.5 g) and cyclohexyl isocyanate (1.2 g) in 70 ml of dry tetrahydrofuran was treated with a catalytic chip of sodium metal and stirred at ambient temperature. After 16 hours, the solution was heated to reflux for 1 hour and thereafter evaporated. The residue was purified by flash chromatography ( silica gel , 16: 1 ethyl acetate/ethanol) to give 2.0 g of an oil. This oil slowly crystallized from petroleum ether to give 1.3 g of a powder, mp 93°–95° C.

ANALYSIS: Calculated for $C_{20}H_{29}N_3O_2$: 69.93% C 8.51% H 12.23% N Found: 69.66% C 8.22% H 12.05% N

EXAMPLE 15

7-Chloro-(3aS-cis)-1,2,3,3a,8,8a-hexahydro-1,3a,8-trimethyl-pyrrolo[2,3-b]indol-5-ol, cyclohexyl carbamate ester A degassed solution containing 7-chloroeseroline (1.5 g) and cyclohexyl isocyanate (1.5 g) in 50 ml of dry tetrahydrofuran was treated with a catalytic chip of sodium metal and stirred at room temperature overnight. This solution was evaporated and the residue purified by column chromatography (neutral alumina, 9:1 ethyl acetate/dichloromethane) to give an oil. This oil was crystallized from ether to give 1.2 g of crystals, mp 154°–156°.

ANALYSIS: Calculated for $C_{20}H_{28}ClN_3O_2$: 63.56% C 7.46% H 11.12% N Found: 63.38% C 7.60% H 10.83% N

EXAMPLE 16

7-Bromo- (3aS-cis)-1,2,3,3a,8,8a-hexahydro-1,3a,8-trimethylpyrrolo[2,3-b]indol-5-ol, cyclohexyl carbamate ester A degassed solution containing 7-bromoeseroline (1.5 g) and cyclohexyl isocyanate (1.5 g) in 60 ml of dry tetrahydrofuran was treated with a catalytic chip of sodium metal and stirred at 50° for 3 hours. This solution was evaporated and the residue purified by column chromatography (alumina, 5:1 ethyl acetate/dichloromethane) to give 2.1 g of powder. This powder was crystallized from ether/petroleum ether to give 1.9 g of crystals, mp 163°–164°.

ANALYSIS: Calculated for $C_{20}H_{28}BrN_3O_2$: 56.68% C 6.68% H 9.95% N Found: 56.98% C 6.60% H 9.88% N

EXAMPLE 17

(3aS-cis)-1,2,3,3a,8,8a-Hexahydro-1,3a,8-trimethyl-pyrrolo[2,3-b]indol-5-ol, 4,4-dimethylcyclohexyl carbamate ester A degassed solution containing eseroline (1.5 g) and 4,4-dimethylcyclohexyl isocyanate (1.5 g) in 60 ml of dry tetrahydrofuran was treated with a catalytic chip of sodium metal, and thereafter stirred at 50° for 4 hours. The solution was evaporated and the residue purified by flash chromatography (silica gel, 9:1 ethyl acetate/methanol) to a foam. This foam crystallized from ether/petroleum ether to give 1.1 g of cubes, mp 98°–99° C.

ANALYSIS: Calculated for $C_{22}H_{33}N_3O_2$: 71.12% C 8.95% H 11.31% N Found: 71.02% C 9.04% H 11.25% N

EXAMPLE 18

(3aS-cis)-1,2,3 ,3a ,8,8a-Hexahydro-1,3a,8-trimethyl-pyrrolo[2,3-b]indol-5-ol, 4-ethylcyclohexyl carbamate ester A degassed solution of eseroline (1.5 g) and 4-ethylcyclohexyl isocyanate (1.5 g) in 70 ml of dry tetrahydrofuran was treated with a catalytic chip of sodium metal and thereafter stirred under reflux for 4 hours. This solution was evaporated and the residue purified by flash chromatography (silica gel, 8:3 ethyl acetate/methanol) to give a powder. This powder was recrystallized from ether to give 1.3 g of crystals, mp 116°–118° C.

ANALYSIS: Calculated for $C_{22}H_{33}N_3O_2$: 71.12% C 8.95% H 11.31% N Found: 70.82% C 8.95% H 11.18% N

EXAMPLE 19

(3aS-cis)-1,2,3,3a,8,8a-Hexahydro-1,3a,8-trimethyl-pyrrolo[2,3-b]indol-5-ol, spiro[5.5]undecan-3-yl carbamate ester A degassed solution containing eseroline (1.5 g) and spiro[5.5]undecan-3-yl-isocyanate (1.9 g) in 60 ml of dry tetrahydrofuran was treated with a catalytic chip of sodium metal. After 4 hours at 65° the solution was evaporated and the residue purified by flash chromatography (silica gel, 9:1 ethyl acetate/methanol). The residue was recrystallized from ether/petroleum ether to give 1.6 g of flakes, mp 110°–112° C.

ANALYSIS: Calculated for $C_{25}H_{37}N_3O_2$: 72.95% C 9.06% H 10.21% N Found: 72.80% C 8.84% H 10.21% N

EXAMPLE 20

(3aS-cis)-1,2,3,3a,8,8a-Hexahydro-1,3a,8-trimethyl-pyrrolo[2,3-b]indol-5-ol, cycloheptyl carbamate ester A degassed solution containing eseroline (1.5 g) and cycloheptyl isocyanate (1.39 g) in 50 ml of dry tetrahydrofuran was treated with a catalytic chip of sodium metal and thereafter stirred under reflux overnight. After 16 hours the solution was evaporated and the residue purified by flash chromatography (alumina, ethyl acetate) to an oil. This oil was crystallized from 1:1 ether/petroleum ether to give 1.6 g of crystals, mp 86°–88° C.

ANALYSIS: Calculated for $C_{21}H_{31}N_3O_2$: 70.55% C 8.74% H 11.75% N Found: 70.62% C 8.77% H 11.66% N

EXAMPLE 21

(3aS-cis)-1,2,3,3a,8,8a-Hexahydro-1,3a,8-trimethyl-pyrrolo-[2,3-b]indol-5-ol, 1,2-dimethylcyclohexen-4-yl carbamate ester A degassed solution containing eseroline (1.5 g) and 1,2-dimethylcyclohexen-4-yl isocyanate (1.5 g) in 60 ml of dry tetrahydrofuran was treated with a catalytic chip of sodium metal, and stirred at room temperature overnight. The solution was evaporated and the residue purified by flash chromatography (silica gel, 9:1 ethyl acetate/methanol) to give a foam. This foam was crystallized from ether/petroleum ether to give 1.2 g of crystals, mp 134°–136° C.

ANALYSIS: Calculated for $C_{22}H_{31}N_3O_2$: 71.51% C 8.45% H 11.37% N Found: 71.21% C 8.51% H 11.32% N

EXAMPLE 22

(3aS-cis)-1,2,3,3a,8,8a-Hexahydro-1,3a,8-trimethyl-pyrrolo[2,3-b]indol-5-ol, cyclohexen-1-yl carbamate ester

A degassed solution containing eseroline (1.5 g) and cyclohexen-1-yl isocyanate (1.5 g) in 70 ml of dry tetrahydrofuran was treated with a catalytic chip of sodium metal and stirred under reflux for 6 hours. The solution was evaporated and the residue purified by flash chromatography (silica gel, 9:1 ethyl acetate/methanol) to give 1.7 g of a powder. This material was recrystallized twice from ether/petroleum ether to give 1.5 g of crystals, mp 133°–134° C.

ANALYSIS: Calculated for $C_{20}H_{27}N_3O_2$: 70.35% C 7.97% H 12.30% N Found: 70.20% C 8.06% H 12.25% N

EXAMPLE 23

(3aS-cis)-1,2,3,3a,8,8a-Hexahydro-1,3a,8-trimethyl-pyrrolo-[2,3-b]indol-5-ol, bicyclo[2.2.1]heptan-2-yl carbamate ester

A degassed solution of eseroline (1.5 g) and bicyclo[2.2.1]heptan-2-yl-isocyanate (1.4 g) in 100 ml of dry tetrahydrofuran was treated with a catalytic chip of sodium metal and thereafter stirred under reflux with a nitrogen blanket overnight. The solution was evaporated and the residue purified by flash chromatography (silica gel, 9:1 ethyl acetate/methanol) to give 1.6 g of a foam which did not crystallize. This foam was heated to 55° at 0.1 mmHg for 5 hours. The resulting melt was pulverized to give 1.6 g of a powder.

ANALYSIS: Calculated for $C_{21}H_{29}N_3O_2$: 70.95% C 8.22% H 11.82% N Found: 70.62% C 8.29% H 11.62% N

EXAMPLE 24

(3aS-cis)-1,2,3,3a,8,8a-Hexahydro-1,3a,8-trimethyl-pyrrolo-[2,3-b]indol-5-ol, 3-chlorophenyl carbamate ester

A degassed solution containing eseroline (1.5 g) and 3-chlorophenyl isocyanate (1.5 g) in 70 ml of dry tetrahydrofuran was treated with a catalytic chip of sodium metal and thereafter stirred under reflux for 4 hours. The solution was evaporated and the residue purified by flash chromatography (silica gel, 9:1 ethyl acetate/methanol) to give an oil. This oil was crystallized from ether/petroleum ether to give 1.2 g of crystals, mp 99°–101° C.

ANALYSIS: Calculated for $C_{20}H_{22}ClN_3O_2$: 64.59% C 5.96% H 11.30% N Found: 64.52% C 5.93% H 11.24% N

EXAMPLE 25

(3aS-cis)-1,2,3,3a8,8a-Hexahydro-1,3a,8-trimethyl-pyrrolo-[2,3-b]indol-5-ol, 4-chlorophenyl carbamate ester

A degassed solution of eseroline (1.5 g) and p-chlorophenyl isocyanate (1.5 g) in 70 ml of dry tetrahydrofuran was treated with a catalytic chip of sodium metal and thereafter stirred under reflux for 16 hours. The solution was evaporated and the residue recrystallized from ether to give 1.3 g of a powder, mp 188°–190° C.

ANALYSIS: Calculated for $C_{20}H_{22}ClN_3O_2$: 64.59% C 5.96% H 11.30% N Found: 64.68% C 6.32% H 11.29% N

EXAMPLE 26

(3aS-cis)-1,2,3,3a,8,8a-Hexahydro-1,3a,8-trimethyl-pyrrolo-[2,3-b]indol-5-ol, 2,6-dimethylphenyl carbamate ester

A degassed solution of eseroline (1.5 g) and 2,6-dimethylphenyl isocyanate (1 g) in 50 ml of dry tetrahydrofuran was treated with a catalytic chip of sodium metal and thereafter stirred under reflux for 16 hours. This solution was evaporated and the residue purified by flash chromatography (alumina, ethyl acetate). The resulting solid was recrystallized from ether/petroleum ether to give 1.3 g of crystals, mp 80°–82° C.

ANALYSIS: Calculated for $C_{22}H_{27}N_3O_2$: 72.29% C 7.44% H 11.49% N Found: 72.07 % C 7.75% H 11.10% N

EXAMPLE 27

(3aS-cis)-1,2,3,3a,8,8a-Hexahydro-1,3a,8-trimethyl-pyrrolo-[2,3-b]indol-5-ol, 4-nitrophenyl carbamate ester

A mixture of eseroline (1.5 g) and 4-nitrophenyl isocyanate (1.6 g) in 70 ml of dry tetrahydrofuran was degassed and treated with a catalytic chip of sodium metal. The mixture was stirred under reflux for 4 hours and thereafter evaporated to a powder. This powder was purified by flash chromatography (silica gel, 19:1 dichloromethane/methanol) and the residue was triturated in ether to give 1.3 g of a powder, mp 199°–201° C.

ANALYSIS: Calculated for $C_{20}H_{22}N_4O_4$: 62.81% C 5.80% H 14.65% N Found: 62.61% C 5.87% H 14.70% N

EXAMPLE 28

(3aS-cis)-1,2,3,3a,8,8a-Hexahydro-1,3a,8-trimethyl-pyrrolo[2,3-b]indol-5-ol, 4-pyridinyl carbamate ester

A mixture of eseroline (1.5 g) and 4-pyridyl isocyanate (1.4 g) in 70 ml of dry tetrahydrofuran was degassed and treated with a catalytic chip of sodium metal. This slurry was heated under reflux with a nitrogen blanket for 16 hours. The resulting solution was evaporated and the residue taken in an aqueous maleic acid solution. This solution was washed with two 100 ml portions of ethyl acetate and the layers were separated. The free base was liberated with saturated sodium bicarbonate and extracted into 200 ml of ethyl acetate. The residue upon evaporation was purified by flash chromatography (silica gel, 4:1, ethyl acetate/methanol) and the concentrated fractions were treated with 100 ml of ether. Upon cooling, 1.2 g of a powder precipitated, mp 163°–165° C.

ANALYSIS: Calculated for $C_{19}H_{22}N_4O_2$: 67.43% C 6.55% H 16.55% N Found: 67.08% C 6.75% H 15.83% N

EXAMPLE 29

(3aS-cis)-1,2,3,3a,8,8a-Hexahydro-1,3a,8-trimethyl-pyrrolo[2,3-b]indol-5-ol, 4-methyl-1-piperazinyl carbamate ester

A degassed solution of eseroline (1.5 g) in 35 ml of dichloromethane was treated in one portion with 1,1'-carbonyldiimidazole (2.2 g) and stirred at room temperature for 1 hour. This solution was then treated with N-methylpiperazine (3.0 g) and stirred at room temperature for 4 additional hours and thereafter evaporated to an oil. This oil was purified by column chromatography (neutral alumina, 4:1 dichloromethane/ethyl acetate) to give 1.9 g of an oil. This oil crystallized from cold petroleum ether to give 1.6 g of crystals, mp 69°–71° C.

ANALYSIS: Calculated for $C_{19}H_{20}N_4O_2$: 66.25% C 8.19% H 16.26% N Found 65.94% C 8.17% H 16.23% N

EXAMPLE 30

(3aS-cis)-1,2,3,3a,8,8a-Hexahydro-1,3a,8-trimethylpyrrolo-[2,3-b]indol-5-ol, 4-morpholinyl carbamate ester A degassed solution of eseroline (1.7 g) in 30 ml of dichloromethane was treated in one portion with 1,1'-carbonyl diimidazole (1.4 g) and stirred at room temperature for 1 hour. This solution was evaporated and the intermediate carbamate was taken up in 60 ml of dry ether and treated with morpholine (5.0 g). After 4 hours of reflux, this solution was evaporated and the residue purified by HPLC (silica gel, 8:1 ethyl acetate/methanol) to give 2.1 g of an oil. This oil was crystallized twice from ether to give 1.6 g of crystals, mp 108°–110°.

ANALYSIS: Calculated for $C_{18}H_{25}N_3O_3$: 65.23% C 7.60% H 12.68% N Found: 65.31% C 7.70% H 12.72% N

EXAMPLE 31

(3 aS-cis)-1,2,3,3a,8,8a-Hexahydro-1,3a,8-trimethylpyrrolo-[2,3-b]indol-5-ol, 4-morpholinyl thiocarbamate ester A degassed solution of eseroline (2.5 g) in 50 ml of dichloromethane was treated with 1,1'-thiocarbonyldiimidazole (3.1 g) in three portions over 5 minutes with stirring. After 45 minutes, this solution was treated with morpholine (4.4 g) and stirred at room temperature for 2 hours. This solution was evaporated and the residue purified by column chromatography (neutral alumina, 9:1 dichloromethane/ethyl acetate) to give 2.8 g of an oil. This oil crystallized from ether to give 2.6 g of crystals, mp 128°–130° C.

ANALYSIS: Calculated for $C_{18}H_{25}N_3O_2S$: 62.22% C 7.25% H 12.09% N Found: 62.18% C 7.42% H 12.05% N

EXAMPLE 32

(3aS-cis)-1,2,3,3a,8,8a-Hexahydro-1,3a,8-trimethylpyrrolo[2,3-b]indol-5-ol, 2-(2,6-dichlorophenylimino)-1-imidazolidinyl-carbamate ester A solution of eseroline (2.5 g) in 60 ml of dichloromethane was treated with solid 1,1'-carbonyldiimidazole (2.7 g) in one portion and stirred at room temperature for 45 minutes. This solution was treated with solid 2-(2,6-dichlorophenylimino)imidazolidine (4.0 g) in two portions over 2 minutes and stirred at room temperature for 6 hours. This solution was evaporated and the residue purified by column chromatography (neutral alumina, 1:1 ethyl acetate/dichloromethane) to give. 4 g of crystals. This material was triturated with ether to give 3.7 g of crystals, mp 165°–167°.

ANALYSIS: Calculated for $C_{23}H_{25}Cl_2N_5O_2$: 58.22% C 5.31% H 14.76% N Found: 58.17% C 5.39% H 14.59% N

EXAMPLE 33

7-Chloro-(3aS-cis)-1,2,3,3a,8,8a-hexahydro-1,3a,8-trimethylpyrrolo[2,3-b]indol-5-ol (7-Chloroeseroline)

A mixture prepared from 2.4 g of 7-chloro-(3aS-cis)-1,2,3,3a,8,8a-hexahydro-1,3a,8-trimethylpyrrolo[2,3-b]-indol-5-ol, methyl carbamate ester in 5 ml of ethanol and 1.0 g of sodium hydroxide in 10 ml of water was degassed and stirred at 40° for 4 hours. The resulting solution was quenched with 100 ml of saturated sodium bicarbonate solution and thereafter extracted with ethyl acetate (2×100 ml). The combined extracts were dried over anhydrous magnesium sulfate, filtered and evaporated to give 1.7 g of powder. An analytical sample was prepared by sublimation (0.1 mmHg, 145°) of the powder to give crystals, mp 152°–154°.

ANALYSIS: Calculated for $C_{13}N_{17}ClN_2O$: 61.77% C 6.78% H 11.08% N Found: 61.73% C 6.74% H 11.02% N

EXAMPLE 34

7-Bromo-(3aS-cis)-1,2,3,3a,8,8a-hexahydro-1,3a,8-trimethylpyrrolo[2,3-b]indol-5-ol (7-Bromoeseroline)

A mixture prepared from 5.1 g of 7-bromo-(3aS-cis)-1,2,3,3a,8,8a-hexahydro-1,3a,8-trimethylpyrrolo[2,3-b]indol-5-ol, methyl carbamate ester in 5 ml of ethanol and 2.0 g of sodium hydroxide in 20 ml of water was degassed and stirred at room temperature for 6 hours. The resulting solution was quenched with 200 ml of saturated sodium bicarbonate solution and thereafter extracted with ethyl acetate (3×100 ml). The combined extracts were dried over anhydrous magnesium sulfate, filtered and evaporated to give 4.1 g of powder. An analytical sample was prepared by sublimation (0.1 mmHg, 160°) of the powder to give crystals, mp 175°–177° C.

ANALYSIS: Calculated for $C_{13}H_{17}BrN_2O$: 52.53% C 5.76% H 9.42% N Found: 52.46% C 5.63% H 9.44% N

EXAMPLE 35

7-Bromo-(3aS-cis)-1,2,3,3a,8,8a-hexahydro-1,3a,8-trimethylpyrrolo[2,3-b]indol-5-ol, 3-chlorophenyl carbamate ester fumarate A degassed mixture of 2.50 g of 7-bromo-(3aS-cis)-1,2,3,3a,8,8a-hexahydro-1,3a,8-trimethylpyrrolo[2,3-b]indol-5-ol, 1.53 g of 3-chlorophenylisocyanate and 0.2 ml of triethylamine in 150 ml of dry benzene was stirred under nitrogen for 5 hours. The solvent was then evaporated in vacuo and the residue was dissolved in 50 ml of ether. To this was added a solution of 1.0 g of fumaric acid in methanol followed by petroleum ether to precipitate the product as the fumarate salt. This was recrystallized from a solvent mixture of methanol/ether/petroleum ether to afford 3.0 g of crystals, mp 170° C., dec.

ANALYSIS: Calculated for $C_{20}H_{21}BrClN_3O_2 \cdot C_4H_4O_4$: 50.85% C 4.45% H 7.41% N Found: 50.68% C 4.75% H 7.48% N

EXAMPLE 36

(3aS-cis)-1,2,3,3a,8,8a-Hexahydro-7-nitro-1,3a,8-trimethylpyrrolo-[2,3-b]indol-5-ol, methyl carbamate ester A degassed solution of 5.00 g of (3aS-cis)-1,2,3,3a,8,8a-hexahydro-1,3a,8-trimethylpyrrolo[2,3-b]indol-5-ol, methyl carbamate ester in 250 ml of acetonitrile was cooled to −23° C. in a bath of carbon tetrachloride/dry ice. A solution of 3.32 g of nitronium tetrafluoroborate in 150 ml of degassed acetonitrile was added dropwise, with stirring, over a period of 10 minutes and the solution was stirred in the cold for an additional 20 minutes. The reaction liquid was then poured into 1.3 liters of dilute sodium bicarbonate/ice mixture. The product was extracted into ethyl acetate (500 ml, 2×300 ml). The combined extracts were washed twice with brine, dried over magnesium sulfate and concentrated to an oil. This was purified by flash chromatography over silica gel using 1% methanol in dichloromethane as eluent. The fractions containing the product were combined and concentrated to an oil which crystallized from a mixed solvent of ether/hexane to give 0.85g of crystals, mp 108°–109° C.

ANALYSIS: Calculated for $C_{15}H_{20}N_4O_4$: 56.24% C 6.29% H 17.49% N Found: 56.07% C 6.47% H 17.24% N

EXAMPLE 37

7-Acetylamino-(3aS-cis)-1,2,3,3a,8,8a-hexahydro-1, 3a,8trimethylpyrrolo[2,3-b]indol-5-ol, methyl carbamate ester A Parr hydrogenation bottle is charged with 3.20 g of (3 aS-cis)-1,2,3,3a,8,8a-hexahydro-7-nitro-1,3a,8-trimethylpyrrolo[2,3-b]indol-5-ol, methyl carbamate ester, 0.3 g of 1% platinum-on-carbon catalyst, 1.53 g of acetic anhydride and 50 ml of degassed tetrahydrofuran. The mixture is shaken at room temperature under an initial hydrogen pressure of 40 psi (pounds per square inch) until uptake of hydrogen ceases. The catalyst is removed by filtration and the filtrate is concentrated in vacuo to afford 7-acetylamino-(3aS-cis)-1,2,3,3a,8,8a-hexahydro-1,3a,8-trimethylpyrrolo[2,3-b]indol-5-ol, methyl carbamate ester.

EXAMPLE 38

7-Bromo-(3aS-cis)-1,2,3,3a,8,8a-hexahydro-1,3a,8-trimethylpyrrolo[2,3-b]indol-5-ol trimethylacetate hydrochloride A solution of 0.69 g of trimethylacetic acid and 1.10 g of 1,1'-carbonyldiimidazole in 100 ml of dry, degassed tetrahydrofuran was refluxed for 1 hour. The reaction mixture was cooled to room temperature, and 2.00 g of 7-bromo-(3aS)-1,2,3,3a,8,8a-hexahydro-1,3a,8-trimethylpyrrolo[2,3-b]indol-5-ol was added. The reaction mixture was stirred overnight and then the solvent was removed in vacuo. The residue was triturated with dichloromethane/petroleum ether to precipitate the imidazole by-product. This was filtered, and the filtrate containing the desired product was concentrated to an oil. The oil was purified by chromatography over neutral alumina using dichloromethane as eluent. The fractions containing the purified product were combined and the solvent was removed to provide 2.1 g of viscous oil. This was dissolved in ether, and the solution was cooled in a dry ice/acetone bath and made acidic by addition of ethereal hydrogen chloride. Addition of petroleum ether caused the product to precipitate. Recrystallization twice from ether/ethanol furnished pure crystals of 7-bromo-(3aS-cis)-1,2,3, 3a,8,8a-hexahydro-1,3a ,8-trimethylpyrrolo[2,3-b]indol-5-ol trimethylacetate hydrochloride, mp 214°–215° C.

ANALYSIS: Calculated for $C_{18}H_{26}BrN_2O_2 \cdot HCl$: 51.63% C 6.50% H 6.69% N Found: 51.60% C 6.26% H 6.71% N

EXAMPLE 39

7-Bromo-(3aS-cis)-1,2,3,3a,8,8a-hexahydro-1,3a,8-trimethylpyrrolo[2,3-b]indol-5-ol diphenylacetate A stirred solution of 2.75 g of diphenylacetic acid and 2.10 g of 1,1'-carbonyldiimidazole in 150 ml of dry, degassed tetrahydrofuran was refluxed until evolution of carbon dioxide gas ceased. The reaction solution was cooled to room temperature and 3.50 g of 7-bromo-(3aS-cis)-1,2, 3,3a,8,8a-hexahydro-1,3a,8trimethylpyrrolo[2,3-b]indol-5-ol was added under nitrogen. The reaction solution was stirred overnight and then the solvent was removed, leaving an oily residue. This was purified by chromatography over neutral alumina using dichloromethane as eluent. The fractions containing the product were combined and concentrated to an oil which crystallized from hexane. This material was recrystallized three times from hexane to give 1.9 of crystals of 7-bromo-(3aS-cis)-1,2,3,3a,8,8a-hexahydro-1,3a, 8- trimethylpyrrolo[2,3-b]indol-5-ol diphenylacetate, mp 93°–95° C.

ANALYSIS: Calculated for $C_{27}H_{27}BrN_2O_2$: 66.00% C 5.54% H 5.70% N Found: 66.01% C 5.68% H 5.64% N

EXAMPLE 40

(3aS-cis)-1-Cyclopropylmethyl-1,2,3,3a,8,8a-hexahydro-5-methoxy- 3a,8-dimethylpyrrolo[2,3-b] indole A stirred solution of 10.9 g of 1,2,3,3a,8,8a-hexahydro-5-methoxy-3a,8-dimethylpyrrolo[2,3-b]indole in 100 ml of dry dimethylformamide is degassed, and then 9.67 g of milled potassium carbonate is added, followed by 5.43 g of (chloromethyl)cyclopropane. The mixture is stirred under nitrogen at 80° overnight. The mixture is cooled to room temperature, and the inorganic solids are removed by filtration and the filtrate is concentrated in vacuo. The residue is purified by column chromatography over neutral alumina using dichloromethane/ethyl acetate mixtures as eluent. The fractions containing the product are combined and concentrated to provide pure 3aS-cis-1-cyclo-propylmethyl-1,2,3, 3a,8,8a-hexahydro-5-methoxy-3a,8-dimethylpyrrolo[2,3-b] indole.

EXAMPLE 41

(3aS-cis)-1,2,3,3a,8,8a-Hexahydro-5-methoxy-1-(2phenylethyl)- 3a,8-dimethylpyrrolo[2,3-b]indole A stirred mixture, under nitrogen, of 8.73 g of 1,2,3,3a, 8,8a-hexahydro-5-methoxy-3a,8-dimethylpyrrolo[2,3-b]-indole, 9.25 g of 2-(bromoethyl)benzene and 8.29 g of milled, anhydrous potassium carbonate in 75 ml of degassed, dry dimethylformamide is heated at 70°–75° for 8 hours and thereafter stirred at room temperature overnight. The reaction mixture is decanted into 1.5 liters of water and the product is extracted into ethyl acetate (2×250 ml). The combined organic extracts are washed twice with saturated aqueous sodium chloride solution, dried over anhydrous sodium sulfate and then concentrated. The residue is subjected to flash chromatography over silica gel using methanol/ethyl acetate mixtures as eluent. The fractions containing the product are combined and concentrated to afford pure (3aS-cis)-1,2,3,3a,8,8a-hexahydro-5-methoxy-1-(2phenylethyl) -3a,8-dimethylpyrrolo[2,3-b]indole.

EXAMPLE 42

(3aS-cis)-1,2,3,3a,8,8a-Hexahydro-5-methoxy-1-(2-propenyl)-3a,8-dimethylpyrrolo[2,3-b]indole To a stirred mixture of 9.82 g of 1,2,3,3a,8,8a-hexahydro-5-methoxy-3a,8-dimethylpyrrolo[2,3-b]indole and 9.67 of milled, anhydrous potassium carbonate in 100 ml of dry, degassed dimethylformamide is added 7.26 g of allyl-bromide in one portion. The mixture is stirred and heated at 65°–70° for 16 hours. The reaction mixture is cooled to room temperature and filtered, and the filtrate is concentrated in vacuo with mild heating. The resulting oil is purified by chromatography over neutral alumina using dichloromethane/ethyl acetate mixtures as eluent. Combination of the appropriate fractions and concentration in vacuo furnishes pure (3aS-cis)-1,2,3,3a,8,8a- hexahydro-5-methoxy-1-(2-propenyl)-3a,8-dimethylpyrrolo[2,3-b]indole.

EXAMPLE 43

(3aS-cis)-5-Ethoxy-1,2,3,3a,8,8a-hexahydro-7-nitro-1,3a,8trimethylpyrrolo[2,3-b]indole A degassed solution, under nitrogen, of 3.70 g of (3aS-cis)-5-ethoxy-1,2,3,3a,8,8a-hexahydro-1,3a,8-trimethylpyrrolo[2,3-b]indole in 50 ml of dry chloroform was treated with 2.00 g of nitronium tetrafluoroborate at a reaction temperature of +10°. After 20 minutes, the reaction was quenched by the addition of ice and saturated sodium bicarbonate solution with vigorous stirring. The organic layer was separated, dried over anhydrous sodium sulfate and concentrated to an oil. This was purified by chromatography over silica gel using ethyl acetate as the eluent. The fractions containing the product were combined and concentrated to an oil which crystallized from hexane to afford crystals of pure (3aS-cis)-5-ethoxy-1,2,3,3a,8,8a- hexahydro-7-nitro-1,3a,8-trimethylpyrrolo[2,3-b]indole, mp 106°–108° C.

ANALYSIS: Calculated for $C_{15}H_{21}N_3O_2$: 61.84% C 7.27% H 14.44% N Found: 61.88% C 7.26% H 14.35% N

EXAMPLE 44

(3aS-cis)-1,2,3,3a,8,8a-Hexahydro-7-nitro-1,3a,8-trimethylpyrrolo[2,3-b]indol-5-ol (7-Nitroeseroline)

A stirred solution, under nitrogen, of 1.85 g of (3aS-cis)-1,2,3,3a,8,8a-hexahydro-7-nitro-trimethylpyrrolo[2,3-b]indol-5ol, methyl carbamate ester in 50 ml of degassed tetrahydrofuran was treated with 0.65 g of potassium t-butoxide. Thirty minutes thereafter the mixture was partitioned between 300 ml of 50 % aqueous ammonium chloride solution and 300 ml of ethyl acetate. The aqueous phase was separated and back-extracted with two 150 ml portions of ethyl acetate. The organic phases were combined, washed with saturated aqueous sodium chloride solution, dried over anhydrous magnesium sulfate and concentrated to an oil. This material was purified by flash chromatography over 50 g of silica gel packed in 1% methanol in dichloromethane, and eluted first with the same solvent mixture (2 liters) and then with 1.5% methanol in dichloromethane (2 liters). The fractions containing the purified product were combined and concentrated in vacuo to 0.8 g of solid. This was recrystallized from ethanol-hexane to provide crystals of pure (3aS-cis)-1,2,3,3a,8,8a-hexahydro-7-nitro-1,3a,8-trimethylpyrrolo[2,3-b]indol-5-ol, mp 170°–171° C. Both NMR and elemental analysis indicated that this compound had crystallized as a solvate with 0.25 mole of ethanol.

ANALYSIS: Calculated for $C_{13}H_{17}N_3O_3 \cdot 0.25CH_3CH_2OH$: 59.00% C 6.78% H 15.29% N Found: 58.98 % C 6.92 % H 15.29 % N

EXAMPLE 45

(3aS-cis)-1,2,3,3a,8,8a-Hexahydro-1-(2-phenylethyl)-3a,8-dimethylpyrrolo[2,3-b]indol -5-ol To a stirred solution under nitrogen of 3.22 g of (3aS-cis)-1,2,3,3a,8,8a-hexahydro-5-methoxy-1-(2-phenylethyl)-3a,8-dimethylpyrrolo[2,3-b]indole in 50 ml of degassed chloroform is added dropwise at 0° C. a solution of 10.1 g of boron tribromide in 50 ml of degassed chloroform. The mixture is stirred for about 3 days at room temperature, cooled to 0° C. and cautiously quenched by the dropwise addition of water. The mixture is stirred vigorously for 0.5 hour, and a sufficient volume of saturated aqueous sodium bicarbonate solution is added to make the system just basic to a pH paper. The organic phase is separated, dried over anhydrous sodium sulfate and concentrated. The residue is Kugelrohr distilled at 0.1 mmHg at an oven temperature of 160°–200° to provide pure (3aS-cis)-1,2,3,3a,8,8a- hexahydro-1-(2-phenylethyl)-3a,8-dimethylpyrrolo[2,3-b]indol-5-ol.

EXAMPLE 46

(3aS-cis)-1,2,3,3a,8,8a-Hexahydro-1-(2-propenyl)-3a,8-dimethylpyrrolo[2,3-b]indol -5-ol This compound is prepared in the same manner as the 1-(2-phenylethyl) derivative of Example 45 except that 2.58 g of (3aS-cis)-1,2,3,3a,8,8a-hexahydro-5-methoxy-1-(2-propenyl)-3a,8-dimethylpyrrolo[2,3-b]indole is reacted as a starting material with 10.1 g of boron tribromide in chloroform.

EXAMPLE 47

(3aS-cis)-1-cyclopropylmethyl-1,2,3,3a,8,8a-hexahydro-3a,8-dimethylpyrrolo[2,3-b]indol-5-ol The title compound is prepared in the same manner as described for the 1-(2-phenylethyl) analog of Example 45 except that 2.72 g of (3aS-cis)-1-cyclopropylmethyl-1,2,3,3a,8,8a-hexahydro-5-methoxy-3a,8-dimethylpyrrolo[2,3-b]indole is reacted as a starting material with 10.1 g of boron tribromide in chloroform.

EXAMPLE 48

(3aS-cis)-1,2,3,3a,8,8a-Hexahydro-1-(2-phenylethyl)-3a,8dimethylpyrrolo[2,3-b]indol-5-ol, methyl carbamate ester A degassed solution of 1.54 g of (3aS-cis)-1,2,3,3a,8,8a-hexahydro-1-(2-phenylethyl)-3a,8-dimethylpyrrolo[2,3-b]indol-5-ol and 0.34 g of methylisocyanate in 60 ml of degassed tetrahydrofuran is treated with a catalytic chip of freshly cut sodium metal and stirred at room temperature overnight (about 16 hours). The volatiles are removed in vacuo and the residue is purified by chromatography over silica gel using mixtures of methanol/ethyl acetate as eluent. The fractions containing the pure product are combined and concentrated in vacuo to provide (3aS-cis)-1,2,3,3a,8,8a-hexahydro-1-(2-phenylethyl)-3a,8-dimethylpyrrolo[2,3-b]indol-5-ol, methyl carbamate ester.

EXAMPLE 49

(3aS-cis)-1,2,3,3a,8,8a-Hexahydro-7-nitro-1,3a,8-trimethylpyrrolo[2,3-b]indol-5-ol acetate fumarate A stirred solution of 2.52 g of 7-nitroeseroline in 25 ml of degassed tetrahydrofuran was cooled under nitrogen to 0° C. and treated with 1.26 g of triethylamine followed by 1.03 g of acetic anhydride. After 30 minutes the solution was decanted into 400 ml of a mixture of ammonium chloride/sodium chloride/ice water. The product was extracted with ethyl acetate (3×200 ml). The combined organic extracts were washed with brine, dried over anhydrous magnesium sulfate, and then concentrated to an oil. This material was purified by flash chromatography over 55 g of silica gel packed in dichloromethane containing 1% diethylamine. Elution with dichloromethane (1.5 liters), followed by 0.5% methanol in dichloromethane (2 liters) brought forth fractions containing the pure product. These were combined and concentrated to 1.66 g of oil. This oil was dissolved in 10 ml of ethanol and then there was added a solution of 0.63 g of fumaric acid in 5 ml of ethanol. The product crystallized as the fumarate salt upon addition of about 15 ml of hexane. This provided 1.62 g of pure crystals, mp 122°–123.5° C.

ANALYSIS: Calculated for $C_{15}H_{19}N_3O_4 \cdot C_4H_4O_4$: 54.15% C 5.50% H 9.97% N Found: 53.86% C 5.48% H 9.64% N

EXAMPLE 50

7-Bromo-(3aS-cis)-1,2,3,3a,8,8a-hexahydro-1,3a,8-trimethylpyrrolo[2,3-b]indol-5-ol acetate hydrochloride A mixture of 3.0 g of 7-bromo-eseroline and 85 mg of sodium bicarbonate in 30 ml of tetrahydrofuran was degassed and kept under $N_2$ at 0° C. Potassium t-butoxide (120 mg) was charged in one portion and the mixture was stirred for 20 minutes. Then 1.08 g of acetic anhydride was added dropwise. After 30 minutes of stirring, thin layer chromatography indicated the reaction was complete. The mixture was quenched with methanol (2 ml) and thereafter concentrated to a solid. This product was extracted into ether (50 ml) and the insolubles were filtered. Treatment with a solution of HCl (generated by acetyl chloride, 800 mg; MeOH, 4 ml; ether, 75 ml) with stirring at 0° C. resulted in crystallization of the hydrochloride salt (2.0 g), mp 218°–221° dec.

ANALYSIS: Calculated for $C_{15}H_{19}BrN_2O_2 \cdot HCl$: 47.95% C 5.37% H 7.46% N Found: 47.66% C 5.35% H 7.57% N

EXAMPLE 51

7-Amino-(3aS-cis)-1,2,3,3a,8,8a-hexahydro-1,3a,8-trimethylpyrrolo[2,3-b]indol-5-ol, methyl carbamate ester A Parr hydrogenation bottle was charged with 2.5 g of (3aS-cis)-1,2,3,3a,8,8a-hexahydro-7-nitro-1,3a,8-trimethylpyrrolo[2,3-b]indol-5-ol, methyl carbamate ester (from Example 36), 0.40 g of 1% platinum-on-carbon catalyst and 200 ml of methanol. The mixture was shaken under 55 psi (pounds per square inch) of hydrogen gas pressure until uptake of hydrogen ceased. The mixture was then filtered to remove the catalyst and the solvent was removed at reduced pressure. The residual oil was purified by chromatography over 20 g of silica gel using 1% methanol in dichloromethane as eluent, followed by 25% methanol in dichloromethane. The fractions containing the purified product were combined and concentrated to afford 1.25 g. This material was dissolved in a mixture of 3 ml of methanol and 7 ml of ether. Hexane was then added dropwise to the turbidity point, and then the mixture was stirred at –10° C. The pure crystals were collected and found to weigh 0.34 g with mp 151°–152.5° C.

ANALYSIS: Calculated for $C_{15}H_{22}N_4O_2$: 62.12% C 7.64% H 19.30% N Found: 61.54% C 7.74% H 18.92% N

We claim:

1. A method of preparing a compound of the formula

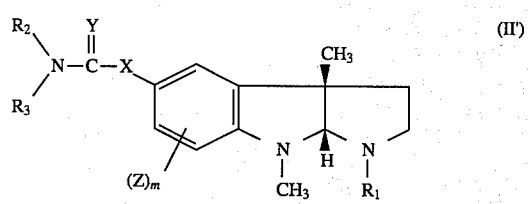

where X is O or S; $R_1$ is H; Y is O or S; $R_2$ is bicycloalkyl, cycloalkenyl, arylloweralkyl, heteroaryl, or heteroarylloweralkyl; $R_3$ is H or alkyl; each Z is independently hydrogen, loweralkyl, halogen, nitro, amino, loweralkylcarbonylamino, arylcarbonylamino, loweralkoxycarbonylamino, or loweralkylamino; and m is 1 or 2, comprising:

reacting a compound of the formula

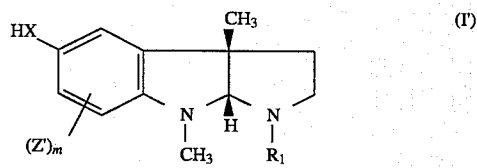

wherein each Z' is independently hydrogen, loweralkyl, halogen, or nitro; $R_1$, X, and m are as defined above; and the nitrogen at the 1-position of formula (II') is protected, with 1,1'-carbonyldiimidazole or 1,1'-thiocarbonyldiimidazole;

reacting the resultant product with a secondary amine of the formula $R_2R_3NH$, wherein $R_2$ and R3 are as defined above, to afford said compound of formula (II'), wherein one or both of the groups $(Z)_m$ is independently hydrogen, loweralkyl, halogen, or nitro, and the nitrogen at the 1-position of formula (II') is protected;

optionally reducing said compound of formula (II'), wherein one or both of the groups $(Z)_m$ is nitro and the nitrogen at the 1-position of formula (II') is protected, to afford said compound of formula (II'), wherein one or both of the groups $(Z)_m$ is amino, and the nitrogen at the 1-position of formula (II') is protected;

optionally reacting said compound of formula (II') wherein one or both of the groups $(Z)_m$ is amino, and the nitrogen at the 1-position of formula (II') is protected, with an acylating agent or alkylating agent to afford said compound of formula (II'), wherein one or both of the groups $(Z)_m$ is loweralkylcarbonylamino, arylcarbonylamino, loweralkoxycarbonylamino, or loweralkylamino, and the nitrogen at the 1-position of formula (II') is protected; and deprotecting the nitrogen at the 1-position of formula (II').

2. A method of preparing a compound of the formula

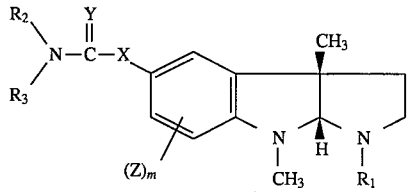

where X is O or S; $R_1$ is H; Y is O or S; $R_2$ is alkyl, cycloalkyl, bicycloalkyl, cycloalkenyl, aryl, arylloweralkyl, heteroaryl or heteroaryllloweralkyl; $R_3$ is H or alkyl; each Z is independently halogen, nitro, amino, loweralkylcarbonylamino, arylcarbonylamino, loweralkoxycarbonylamino, or loweralkylamino; and m is 1 or 2, comprising:

reacting a compound of the formula

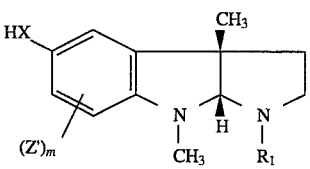

wherein each Z' is independently halogen or nitro; $R_1$, X, and m are as defined above; and the nitrogen at the 1-position of formula (II') is protected with 1,1'-carbonyldiimidazole or 1,1'-thiocarbonyldiimidazole;

reacting the resultant product with a secondary amine of the formula $R_2R_3NH$, wherein $R_2$ and $R_3$ are as defined above, to afford said compound of formula (II'), wherein one or both of the groups $(Z)_m$ is halogen or nitro and the nitrogen at the 1-position of formula (II') is protected;

optionally reducing said compound of formula (II'), wherein one or both of the groups $(Z)_m$ is nitro and the nitrogen at the 1-position of formula (II') is protected, to afford said compound of formula (II'), wherein one or both of the groups $(Z)_m$ is amino and the nitrogen at the 1-position of formula (II') is protected;

optionally reacting said compound of formula (II'), wherein one or both of the groups $(Z)_m$ is amino, and the nitrogen at the 1-position of formula (II') is protected, with an acylating agent or alkylating agent to afford said compound of formula (II'), wherein one or both of the groups $(Z)_m$ is loweralkylcarbonylamino, arylcarbonylamino, loweralkoxycarbonylamino, or loweralkylamino, and the nitrogen at the 1-position of formula (II') is protected; and deprotecting the nitrogen at the 1-position of formula (II').

3. A method of preparing a compound of the formula

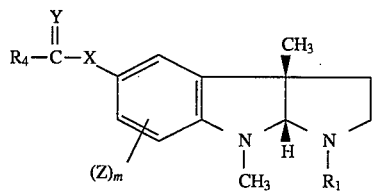

wherein X is O or S; $R_1$ is H; Y is O or S; $R_4$ is H, loweralkyl, aryl, aryllloweralkyl, diarylloweralkyl or heteroaryl; each Z is independently hydrogen, loweralkyl, halogen, nitro, —NH$_2$, loweralklycarbonylamino, arylcarbonylamino, loweralkoxycarbonylamino, or loweralkylamino; and m is 1 or 2, comprising:

reacting a carboxylic acid or thiocarboxylic acid of the formula $R_4CYOH$, wherein Y is O or S, with 1,1-carbonyldiimidazole or 1,1'-thiocarbonyliimidazole, and thereafter adding to the reaction mixture a phenol or thiophenol compound of the formula

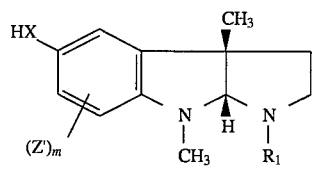

wherein each Z' is independently hydrogen, loweralkyl, halogen, or nitro; $R_1$, X, and m are as defined above; and the nitrogen at the 1-position of formula (III') is protected, to afford said compound of formula (III'), wherein one or both of the groups $(Z)_m$ is independently hydrogen, loweralkyl, halogen, or nitro, and the nitrogen at the 1-position of formula (III') is protected;

optionally reducing said compound of formula (III'), wherein one or both of the groups $(Z)_m$ is nitro and the nitrogen at the 1-position of formula (III') is protected, to afford said compound of formula (III'), wherein one or both of the groups $(Z)_M$ is amino and the nitrogen at the 1-position of formula (III') is protected;

optionally reacting said compound of formula (III'), wherein one or both of the groups $(Z)_m$ is amino, and the nitrogen at the 1-position of formula (III') is protected, with an acylating agent or alkylating agent to afford said compound of formula (III'), wherein one or both of the groups $(Z)_m$ is loweralkylcarbonylamino, arylcarbonylamino, loweralkoxycarbonylamino, or loweralkylamino, and the nitrogen at the 1-position of formula (III') is protected; and deprotecting the nitrogen at the 1-position of formula (III').

4. A method of preparing a compound of the formula

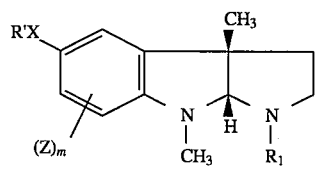

where X is O or S; R' is loweralkyl; $R_1$ is hydrogen; each Z is independently halogen, nitro, —NH$_2$, loweralkylcarbonylamino, arylcarbonylamino, loweralkoxycarbonylamino, or loweralkylamino; and m is 1 or 2, comprising:

reacting a phenol or thiophenol of the formula

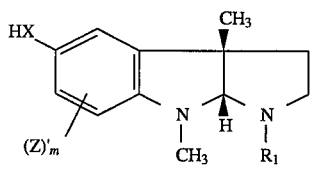

wherein each Z' is independently halogen or nitro; $R_1$, X, and m are as defined above; and the nitrogen at the 1-position of formula (IV') is protected, with a loweralkyl p-toluenesulfonate, to afford said compound of formula (IV'), wherein one or both of the groups $(Z)_m$ is halogen or nitro, and the nitrogen at the 1-position of formula (IV') is protected;

optionally reducing said compound of formula (IV'), wherein one or both of the groups $(Z)_m$ is nitro and the nitrogen at the 1-position of formula (IV') is protected, to afford said compound of formula (IV'), wherein one or both of the groups $(Z)_m$ is amino, and the nitrogen at the 1-position of formula (IV') is protected;

optionally reacting said compound of formula (IV') wherein one or both of the groups $(Z)_m$ is amino, and the nitrogen at the 1-position of formula (IV') is protected, with an acylating agent or alkylating agent to afford said compound of formula (IV'), wherein one or both of the groups $(Z)_m$ is loweralkylcarbonylamino, arylcarbonylamino, loweralkoxycarbonylamino, or loweralkylamino, and the nitrogen at the 1-position of formula (IV') is protected; and deprotecting the nitrogen at the 1-position of formula (IV').

* * * * *